United States Patent
Gourvest et al.

[11] Patent Number: 5,827,887
[45] Date of Patent: Oct. 27, 1998

[54] BIPHENYL COMPOUNDS

[75] Inventors: Jean-François Gourvest, Claye-Souilly; Dominique Lesuisse, Paris; Jean-Georges Teutsch, Pantin, all of France

[73] Assignee: Roussel Uclaf, France

[21] Appl. No.: 690,681

[22] Filed: Jul. 31, 1996

[30] Foreign Application Priority Data

Aug. 8, 1995 [FR] France .................................. 95 09618

[51] Int. Cl.$^6$ ........................ C07C 235/18; A61K 31/19
[52] U.S. Cl. ........................................... 514/563; 562/451
[58] Field of Search ............................ 562/451; 514/563

[56] References Cited

U.S. PATENT DOCUMENTS 5,356,893  10/1994  Bradshaw ............................ 514/227.2

FOREIGN PATENT DOCUMENTS

| 0296802 | 12/1988 | European Pat. Off. . | |
|---|---|---|---|
| 0533266 | 3/1993 | European Pat. Off. . | |
| 533266 | 3/1993 | European Pat. Off. ............ | 514/227.2 |
| 2276160 | 9/1994 | United Kingdom . | |
| 2276161 | 9/1994 | United Kingdom . | |
| PCT/JP 92-00981 | 8/1992 | WIPO . | |
| PCT/EP/ 9300867 | 4/1993 | WIPO . | |
| PCT/JP 93-00710 | 5/1993 | WIPO . | |
| PCT/EP 95 00900 | 3/1995 | WIPO . | |

OTHER PUBLICATIONS

Journal of Organic Chemistry, vol. 57, Jul. 17, 1992, No. 15.
Chem. Abstracts, vol. 111, 1989 p. 322.
Chemische Berichte, vol. 113, No. 11, 1980 Weinheim DE.
Noncondensed Aromatics, vol. 92, 1980 p. 751.
Chem. Abstracts, vol. 52, 1958 (2 pages).

*Primary Examiner*—Robert Gerstl
*Attorney, Agent, or Firm*—Bierman, Muserlian and Lucas

[57] ABSTRACT

Novel compounds of the formula

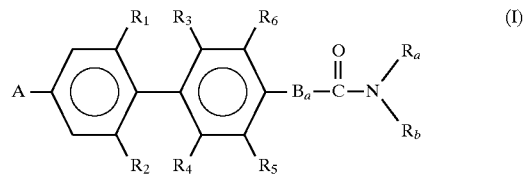

wherein the substituents are defined as in the application and their salts with non-toxic, pharmaceutically acceptable acids and bases having 5-α-reductase inhibiting activity and a process and intermediates for their preparation.

23 Claims, No Drawings

BIPHENYL COMPOUNDS

OBJECTS OF THE INVENTION

It is an object of the invention to provide the novel biphenyl compounds of formula I and their non-toxic pharmaceutically acceptable addition salts and a process and intermediates for their preparation.

It is another object of the invention to provide novel pharmaceutical compositions and a method of inhibiting 5-α-reductase in warm-blooded animals Those and other objects and advantages of the invention will become obvious from the following detailed description.

THE INVENTION

The novel biphenyl compounds of the invention are selected from the group consisting of a compound of the formula

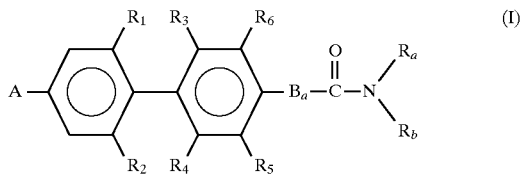

wherein A is selected from the group consisting of carboxy, —CN, —NO$_2$, HONHCO— and a nitrogen heterocycle B$_a$, is selected from the group consisting of a) single bond, b) —(CH$_2$)$_n$—, n is an integer from 1 to 6, c) —(CH$_2$)$_{n-1}$—CH(Alk)-, Alk is alkyl of 1 to 6 carbon atoms and d) —O—(CH$_2$)$_{n'}$—, n' being an integer from 1 to 6, R$_a$ and R$_b$ are individually selected from the group consisting of hydrogen, alkyl of 1 to 8 carbon atoms, acyl of organic carboxylic acid of 1 to 12 carbon atoms, phenyl, benzyl, diphenylmethyl and trityl or together with the nitrogen they are attached form an optionally unsaturated 5 to 6 member heterocycle optionally containing a second —S—, —NH or —O—, R$_1$, R$_2$, R$_3$, R$_4$, R$_5$ and R$_6$ are individually selected from the group consisting of hydrogen, halogen, optionally substituted alkyl of 1 to 8 carbon atoms, alkoxy and alkylthio of 1 to 8 carbon atoms, —NO$_2$, —CN, —CF$_3$, —NH$_2$, mono and dialkyl amino with alkyl of 1 to 8 carbon atoms and

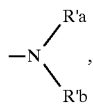

R'a and R' together with the nitrogen to which they are attached form an optionally unsaturated 5 to 6 member nitrogen heterocycle optionally containing a second nitrogen or —O— or —S— optionally substituted with alkyl of 1 to 4 carbon atoms or R$_4$ and R$_5$ form —CH=CH—CH=CH— and their non-toxic, pharmaceutically acceptable salts with acids or bases.

R$_1$, R$_2$, R$_3$, R$_4$, R$_5$ or R$_6$ can be alkyl of 1 to 8 carbon atoms optionally substituted by at least one member of the group consisting of halogen, hydroxy, alkoxy of 1 to 4 carbon atoms, alkylthio of 1 to 4 carbon atoms, acyloxy of an organic carboxylic acid of 1 to 12 carbon atoms, alkoxycarbonyl of 2 to 12 carbon atoms, acyl of an organic carboxylic acid of 1 to 12 atoms, amino, alkylamino or dialkylamino in which each alkyl has 1 to 8 carbon atoms, —NR"$_a$R"$_b$ wherein R"$_a$ and R"$_b$ form together with the nitrogen atom to which they are attached an optionally unsaturated nitrogen 5 to 6 ring heterocycle optionally containing a second heteroatom selected from nitrogen, oxygen, and sulfur.

Examples of alkyl of 1 to 8 carbon atoms are methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl-pentyl, 3-ethylpentyl, n-octyl, 2,2-dimethylhexyl, 3,3-dimethylhexyl, 3-methyl-3-ethylpentyl. Preferably it is methyl, ethyl, propyl or isopropyl.

Examples of acyl of 1 to 12 atoms are formyl, acetyl, propionyl, butyryl, isobutyryl, valeryl, isovaleryl, oxalyl, succinyl or pivaloyl.

When R$_a$ and R$_b$, R'$_a$ and R'$_b$ or R"$_a$ and R"$_b$ form together with the nitrogen atom to which they are attached a heterocycle with 5 or 6 ring members, it is either a saturated heterocycle, such as pyrrolidine or piperidine, or an unsaturated heterocycle such as pyrrole or pyridine, or a saturated or unsaturated heterocycle optionally containing another heteroatom chosen from nitrogen, oxygen and sulfur such as morpholine, piperazine or pyrimidine, the second nitrogen atom being optionally substituted by alkyl, preferably methyl, ethyl, propyl or isopropyl. R$_a$ and R$_b$ preferably form together with the nitrogen to which they are attached a saturated heterocycle with 5 or 6 ring members optionally containing a second heteroatom. When A is a nitrogen heterocycle, it is preferably the tetrazole radical.

Examples of alkoxy of 1 to 8 carbon atoms are methoxy, ethoxy, propoxy, and butoxy and examples of alkylthio of 1 to 8 carbon atoms are methylthio, ethylthio, propylthio or butylthio.

Examples of acyloxy of 1 to 12 carbon atoms are the derivative of a saturated or unsaturated aliphatic or cycloaliphatic acid and in particular, an alkanoic acid such as acetic acid, propionic acid, butyric acid or isobutyric acid, valeric acid or undecyclic acid, a cycloalkylcarboxylic or cycloalkylalkanoic acid such as cyclopropyl, cyclopentyl or cyclohexyl-carboxylic acids, or cyclopentyl- or cyclohexyl-acetic acid or propionic acid or butyric acid.

Examples of halogen are fluorine, chlorine, bromine or iodine.

Examples of salts of the compounds of formula I, i.e. to the salts formed when the compounds of formula I contain an amino function are the following acids: hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene or p-toluene sulfonic acid and arylcarboxylic acids, or when the compounds of formula (I) contain an acid function, salts with alkali metals or alkaline-earth metals or an optionally substituted ammonium. Preferably, it is the sodium salt.

Among the preferred compounds of formula I are those wherein A is carboxy and B$_a$ is a single bond or —CH$_2$— or —OCH$_2$—, those wherein A is tetrazolyl and B$_a$ is a single bond, —CH$_2$—, —CHCH$_3$— or —OCH$_2$—, those wherein R$_a$ and R$_b$ are alkyl of 1 to 8 carbon atoms, preferably methyl, ethyl, n-propyl or is a propyl, most preferably isopropyl, those wherein R$_a$ is hydrogen and R$_b$ is trityl, those wherein R$_1$, R$_2$, R$_3$, R$_4$, R$_5$ and R$_6$ are individually selected from the group consisting of hydrogen, chlorine, iodine, bromine, fluorine, methyl, ethyl, propyl, isopropyl, cyano, nitro, amino, dimethylamino, ethoxy, methylthio, ethylthio and trifluoromethyl, or R$_4$ and R$_5$, form together —CH=CH—CH=CH—, those wherein A is carboxy, $B_a$ is a single bond or —CH$_2$— or —OCH$_2$— and $R_a$ and $R_b$ are alkyl of 1 to 8 carbon atoms or $R_a$ is hydrogen and $R_b$ is trityl and $R_1$, $R_2$, $R_3$, $R_4$, $R_5$ and $R_6$ are individually selected from the group consisting of hydrogen, chlorine, iodine, bromine, fluorine, methyl, ethyl, propyl, isopropyl, cyano, nitro, amino, dimethylamino, methoxy, ethoxy, methylthio, ethylthio and trifluoromethyl and those wherein A is carboxy and $B_a$ is —OCH$_2$— and their addition salts.

Examples of specific preferred compounds of formula I are

4'-[2-[bis-(isopropyl)-amino]-2-oxoethoxy)-(1,1'-biphenyl)-4-carboxylic acid,

4'-[2-[bis-(isopropyl)-amino]-2-oxoethoxy]-3',5'-bis-(isopropyl)-(1,1'-biphenyl)-4-carboxylic acid, 4'-[2-[bis-(isopropyl)-amino]-2-oxoethoxy]-3'-fluoro-5'-nitro-(1,1'-biphenyl)-4-carboxylic acid, 4'-[2-oxo-2-([tribenzyl)-amino]-ethoxy]-(1,1'-biphenyl)-4-carboxylic acid, 3'-fluoro-5'-nitro-4'-[2-oxo-2-[(tribenzyl)-amino]-ethoxy]-(1,1'-biphenyl)-4-carboxylic acid, 4'-[2-[bis-(isopropyl)-amino]-2-oxoethoxy]-2'-ethyl-(1,1'-biphenyl)-4-carboxylic acid, 4'-[2-[bis-(isopropyl)-amino)-2-oxoethoxy]-3'-ethyl-(1,1'-biphenyl)-4-carboxylic acid, 4'-[2-[bis-(isopropyl)-amino]-2-oxoethoxy]-2-chloro(1,1'-biphenyl)-4-carboxylic acid, 4'-[2-[bis-(isopropyl)-amino]-2-oxoethoxy]-2-(trifluoromethyl)-(1,1'-biphenyl)-4-carboxylic acid and their addition salts.

The novel process of the invention for the preparation of a compound of formula I comprises reacting a compound of the formula

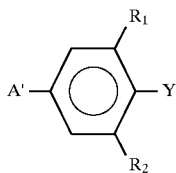

(II)

in the presence of a catalyst with a compound of the formula

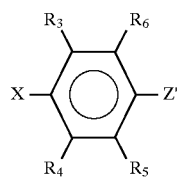

(III)

wherein $R_1$, $R_2$, $R_3$, $R_4$, $R_5$ or $R_6$ are as defined above, A' is selected from the group consisting of optionally protected formyl, optionally esterified carboxy, cyano, nitrogen heterocycle, nitro, methyl or optionally protected —CH$_2$OH, Z' is $B_a$—CO—NR$_a$R$_b$ or an optionally protected OH and in which:

(a) either Y is B(OH)$_2$ or SnBu$_3$ and X is OSO$_2$CF$_3$, bromine or iodine, (b) or Y is OSO$_2$CF$_3$, bromine or iodine, and X is B(OH)$_2$ or SnBu$_3$, (c) or Y is iodine and X is chlorine, (d) or Y is chlorine and X is iodine, (e) or Y is bromine and X is hydrogen, (f) or Y is hydrogen and X is bromine to obtain a compound of the formula

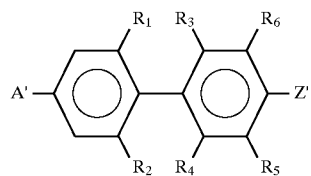

(I')

in which $R_1$, $R_2$, $R_3$, $R_4$, $R_5$, $R_6$, A' and Z' are as defined previously, being able, if appropriate, to correspond to certain products of formula I, which product of formula I' if desired or if necessary is subjected in any appropriate order to one or, if appropriate, several of the following reactions in order to obtain the product of formula I:

oxidation of formyl of A', oxidation of methyl of A', oxidation of CH$_2$OH of A', saponification of the ester of A', the action of azido terbutyl tin (Bu$_3$SnN$_3$), then of hydrochloric acid when A' is cyano to obtain the product of formula I in which A is a tetrazolyl, the action of benzylhydroxylamine hydrochloride when A' is CO$_2$H to obtain the products of formula I in which A is CONHOH, protection of CH$_2$OH, CHO, or CO$_2$H of A', protection of OH of Z', deprotection of protected CH$_2$OH, CHO, or CO$_2$H of A', deprotection of protected OH of Z', the action of Hal-(CH$_2$)$_n$—CO—NR$_a$R$_b$ when Z' is —OH, the action of Alk$_1$—X in the presence of a strong base when Z or Z' is (CH$_2$)$_n$—CO—NR$_a$R$_b$ to obtain the products of formula I in which A is (CH$_2$)$_{n-1}$—CH (Alk$_1$)—CO—NR$_a$R$_b$, total or partial reduction of NO$_2$ of $R_1$, $R_2$, $R_3$, $R_4$, $R_5$ or $R_6$, substitution of NH$_2$ of $R_1$, $R_2$, $R_3$, $R_4$, $R_5$, R6 by bromine or iodine, and salification by an acid or a base.

The formation of the biphenyls of formula I' by coupling the aromatic compound of formula II with the aromatic compound of formula III is carried out:

either in the presence of a catalyst selected from the group consisting of palladium in the cases where:

(a) Y is B(OH)$_2$ or SnBu$_3$ and X is OSO$_2$CF$_3$, bromine or iodine, (b) Y is OSO$_2$CF$_3$ or bromine or iodine and X is B(OH)$_2$ or SnBu$_3$, and thus can be carried out under the conditions described in the following articles when X or Y is B(OH)$_2$:

Huth et al, Tetrahedron (1989), Vol. 45 p. 6679: Conditions: Na$_2$CO$_3$ 2M/Pd (PΦ$_3$)$_4$/Toluene/LiCl/EtOH/Δ.

Stille et al., Ang. Chem. Int. Ed. (1986), Vol. 25, p. 508: Conditions: Pd(PΦ$_3$)$_4$/LiCl/Dioxane/Oh-e et al, J. Org. Chem. (1993), Vol. 58, p. 2201–2208: Conditions: K$_3$PO$_4$/KBr/Pd(PΦ$_3$)$_4$/Dioxane/Δ

Suzuki et al., Synlett (1992), p. 208 Conditions: Pd(PΦ$_3$)$_4$/Ba(OH)$_2$/DMEaq;

or when X or Y is SnBu$_3$ under the conditions described in the following articles:

Still et al, J. Am. Chem. Soc. (1987), pp. 5478–5480 or by Farina, J. Org. Chem. (1993), Vol. 58, p. 5434; or in the presence of copper in the case where:

(c) Y is iodine and X is chlorine, (d) Y is chlorine and X is iodine,
and thus can be carried out under the conditions described in the following article:

Fanta, Chem. Rev. (1964), Vol. 38, p. 139 or Synthesis, (1974), p. 9: Conditions: Cu/DMF/120° C.;
or in the presence of a strong base and $ZnCl_2$, then of a catalyst selected from derivatives of palladium in the case where:
(e) Y is bromine and X is hydrogen,
(f) Y is hydrogen and X is bromine,
and thus can be carried out under the following conditions:
1) nBuLi/THF/–78° C.
2) $ZnCl_2$
3) $ArBr/Pd(P\Phi_3)_4/\Delta$
4) HCl/MeOH.

The orthometallation reactions are described for example in the following documents: KRESS, Synthesis, (1983), p. 803, IWAO, J. Org. Chem. (1990), Vol. 55, p. 3623. Furthermore, the exchange reaction with $ZnCl_2$ followed by a coupling reaction has been described by Negishi in J. Org. Chem., (1977), Vol. 42, p. 182.

The oxidation reaction of CHO of A' into $CO_2H$ can be carried out by the action of Jones reagent (chromic acid/sulfuric acid) in a neutral solvent such as acetone, by the action of silver oxide ($Ag_2O$) in tetrahydrofuran and 2N sodium hydroxide or by the action of sodium chlorite in the presence of aminosulfonic acid.

The oxidation reaction of methyl of A' into $CO_2H$ can be carried out by the action of $KMnO_4$ in a basic medium. The oxidation reaction of $CH_2OH$ of A' into $CO_2H$ can be carried out by the action of Jones' reagent in acetone.

The saponification reaction of an ester function of A' into the corresponding acid is carried out for example by the action of an alkaline base such as sodium hydroxide or potassium hydroxide in tetrahydrofuran or a lower alcohol such as methanol or ethanol.

The action of $Bu_3SnN_3$, then of HCl when A' is cyano to obtain the product of formula I in which A is tetrazolyl is carried out by the reaction described by Barraclough et al. in J. Chem. Soc. Perkin I, (1989), p. 1815.

The action of benzylhydroxylamine hydrochloride when A' is $CO_2H$ to obtain the products of formula I in which A is CONHOH is carried out in the presence of a base such as triethylamine, hydroxy-benzotriazole and dicyclohexyl carbodiimide.

When Z' is OH optionally protected by a protective group P, P is preferably alkyl of 1 to 4 carbon atoms, benzyl, $R_C R_D R_E Si$, in which $R_C$, $R_D$ and $R_E$, are individually alkyl of 1 to 4 carbon atoms or aryl and particularly phenyl.

Furthermore, the $CO_2H$ of A' can be esterified, the formyl of A' can be protected in the form of an acetal such as dioxolane by the action of glycol in the presence of p-toluene sulfonic acid, the $CH_2OH$ of A' can be protected in the form of a tetra-hydropyranyloxy by the action of dihydropyran.

The deprotection reactions are standard deprotection methods known to a man skilled in the art. A fairly comprehensive review is found in Protective groups in Organic Synthesis, T. W. Greene, John Wiley & Sons, (1981)

By way of example, the deprotection reactions when P is methyl can be carried out by the action of tribromoborane in dichloromethane or hydrochloric acid in pyridine, the deprotection reactions when P is benzyl can be carried out by the action of hydrogen in the presence of palladium on charcoal in ethyl acetate or by the action of trifluoroacetic acid, the deprotection reactions when P is tertbutyldiphenylsilyl can be carried out by the action of ammonium tetrabutyl fluoride in solution in tetrahydrofuran.

When P is tetrahydropyranyl, the deprotection is carried out in the presence of an aqueous acid in an alcoholic solvent and preferably by the action of hydrochloric acid in methanol.

The action of Hal-$(CH_2)_n$—CO—$NR_aR_b$, Hal is halogen and preferably bromine, when Z' is hydroxyl, is carried out in the presence of sodium hydroxide in an aprotic dipolar solvent such as dimethylsulfoxide or in the presence of potassium or sodium hydride in dimethylformamide or dimethylsulfoxide.

The action of $Alk_1$—X in the presence of a strong base such as lithium diisopropylamide (LDA), when A or A' is $(CH_2)_n$—CO—$NR_aR_b$ allows the products of formula I in which A is $(CH_2)_{n-1}$—CH($Alk_1$)—CO—$NR_aR_b$ to be obtained.

The reduction reaction of $NO_2$ which can be $R_1$, $R_2$, $R_3$, $R_4$, $R_5$ or $R_6$ into $NH_2$ can be carried out by the action of tin dichloride in ethanol under reflux and the monoreduction reaction is preferably carried out by the action of cyclohexene in the presence of palladium dihydroxide in ethanol under reflux.

The substitution reaction of $NH_2$ of $R_1$, $R_2$, $R_3$, $R_4$, $R_5$ or $R_6$ by bromine is preferably carried out by the action of hydrobromic acid in the presence of sodium nitrite and copper bromide in water at 0° C.

The substitution reaction of $NH_2$ of $R_1$, $R_2$, $R_3$, $R_4$, $R_5$ or $R_6$ by iodine is preferably carried out by the action of potassium iodide in the presence of sodium nitrite and sulfuric acid.

The salification can be carried out under the usual conditions. For example, the operation is carried out in the presence of ethanolic sodium hydroxide. A sodium salt can also be used such as sodium or potassium carbonate or bicarbonate.

Similarly, salification by an acid is carried out under the usual conditions. For example, the operation is carried out with hydrochloric acid in an ethereal solution.

A preferred embodiment of the process of the invention to prepare a compound of formula I comprises reacting a compound of the formula

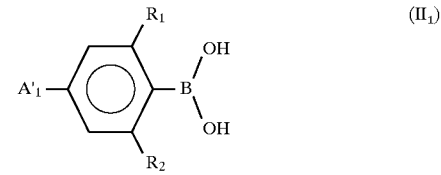

(II$_1$)

in the presence of a catalyst selected from the derivatives of Pd with a compound of the formula

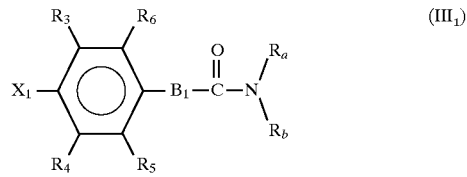

(III$_1$)

in which $R_a$, $R_b$, $R_1$, $R_2$, $R_3$, $R_4$, $R_5$ or $R_6$ are as defined above, A'$_1$ is formyl or optionally esterified carboxy, $X_1$ is $OSO_2CF_3$, bromine or iodine and $B_1$ is a single bond, —$CH_2$— or —$OCH_2$— to obtain a product of the formula

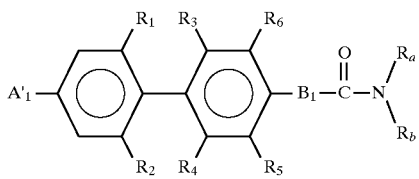
(I'₁)

in which $R_a$, $R_b$, $R_1$, $R_2$, $R_3$, $R_4$, $R_5$, $R_6$, $B_1$ and $A'_1$ are as defined previously, being able, if appropriate, to correspond to certain products of formula I, which product of formula I'₁ if desired or if necessary is subjected in any appropriate order to one or, if appropriate, several of the following reactions to obtain the product of formula I:

oxidation of formyl of $A'_1$, saponification of the ester of $A'_1$, total or partial reduction of $NO_2$ of $R_1$, $R_2$, $R_3$, $R_4$, $R_5$ or $R_6$, substitution of $NH_2$ of $R_1$, $R_2$, $R_3$, $R_4$, $R_5$, $R_6$ by bromine or iodine, and salification by an acid or a base.

The 5-α-reductase inhibiting compositions of the invention are comprised of an 5-α-reductase inhibiting amount of a compound of the formula I and its non-toxic, pharmaceutically acceptable salts and an inert pharmaceutical carrier. The compositions may be in the form of tablets, dragees, capsules, granules, suppositories, injectable preparations, pessaries, ointments, creams, gels and patches prepared by the usual methods.

The active ingredients can be incorporated with excipients usually employed in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifiers or preservatives.

The compositions respond in a significant way as an inhibitor of the testosterone enzyme, 5-α-reductase, which is a key enzyme in the biosynthesis of certain androgens, particularly 4,5-α-dihydrotestosterone (DHT). For the first time, it has been determined that biphenyl compounds, therefore non-steroidal compounds, act in a significant way as an inhibitor of the testosterone 5-α-reductase enzyme which was in no way foreseeable from the prior art.

The prior art teaches that apart from products in the steroid series such as Finasteride (MK906), there exist some derivatives which are inhibitors of the testosterone enzyme 5-α-reductase, in the indole or quinoline series By way of example, there can be mentioned:

In the Quinoline series:

1,2,3,4,5,6-hexahydrobenzo[f]quinolin-3-one described in Patent Application EP-531026, Trans-DL-8-chloro-4-methyl-1,2,3,4,4a,5,10b-octahydro-benzo[f] quinolin-3-ones (LY191704) described in Patent Application EP-532190. In the Indole series: 4-[3-[4-[1-(4-isobutylphenyl) pentyloxy]benzoyl]indol-1-yl]butyric acid described in Patent Application W09305019, and (R,S)-4-(3-[4-(2-methylpropyl)phenyl]ethoxy)-phenyl-ethanoyl]indol-1-yl)butanoic acid described in Patent Application WO9302051.

The compounds of formula I have a specific activity as an inhibitor of 5-α-reductase. 5-α-reductase is an enzyme responsible for the conversion of testosterone into 5-α-dihydrotestosterone (DHT), which has a greater affinity than testosterone for the receptor of androgens (RA). This hormone is essential, in the male, for the in utero development of the external sexual organs and from puberty, for the appearance of certain secondary sexual characteristics (piteous system, face and body).

5-α-reductase is essentially found in the prostate and in the skin, where it appears that testosterone must be converted into DHT in order to be active. An excess of DHT can be responsible for acne or androgenic alopecia, hirsutism in women, and its accumulation at the level of the prostate, for benign hyperplasia (BHP) or cancer of the prostate. It is estimated that 80% of men who are older than 80 have an BHP, and 70% have cancerous foci.

The inhibition of this enzymatic stage in the steroid metabolism entails a fall in the level of DHT in vivo. This reduction in the level of DHT has the effect of reducing the size of the prostate in man and therefore has a beneficial effect in the treatment of benign hyperplasia of the prostate, cancer of the prostate, and certain androgen-dependent illnesses.

A treatment inhibiting 5-α-reductase is therefore very useful and does not have the disadvantages of an antiandrogen which blocks the receptor. This 5-α-reductase inhibitory property therefore makes the compounds of formula I suitable for use in the treatment of disorders linked to virilism, particularly that of benign hyperplasia of the prostate, cancer of the prostate, acne, androgenic alopecia, seborrhea, or also feminine hirsutism. The compounds are useful for the treatment of disorders linked to The novel method of the invention for inhibiting 5-α-reductase in warm-blooded animals, including humans, comprises administering to warm-blooded animals a 5-α-reductase inhibiting effective amount of a compound of formula or its non-toxic, pharmaceutically acceptable salts. The compounds may be administered orally, rectally, parenterally or topically; i.e transdermically. The usual daily dose is 5 to 100 mg/kg depending upon the conditions treated, the method of administration and the specific compound used.

The products of formula II in which Y is $OSO_2CF_3$ or the products of formula III in which X is $OSO_2CF_3$ are obtained from the corresponding alcohols of the formulae:

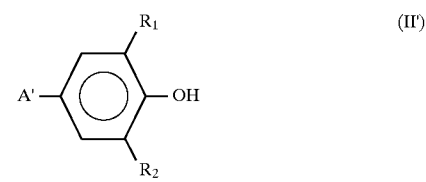
(II')

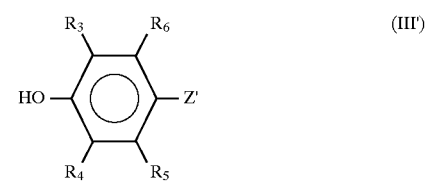
(III')

by the action of trifluoromethanesulfonic anhydride in pyridine at 0° C. according to the method described by Scott et al, J. Am. Chem. Soc. (1986), Vol. 108, p. 3033.

The products of formula II with Y as iodine or the products of formula III with X as iodine, can be obtained by ortho-metallation from the corresponding non-iodated aromatic products of formulae II" and III", respectively, corresponding to the products of formula II with Y as hydrogen and to the products of formula III with X as hydrogen respectively:

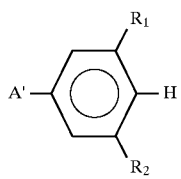

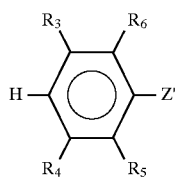

particularly by the action of N-iodosuccinimide or iodine in the presence of a strong base such as n-butyllithium in tetrahydrofuran at −78° C.

The products of formula II with Y as $B(OH)_2$ or (III) with X as $B(OH)_2$ can be obtained from the products of formula II''' or III''' respectively, corresponding to the product of formula II with Y as bromine and to the product of formula III with X as bromine, it being understood that regarding the product of formula III''', the OH which can be Z' is protected as described previously,

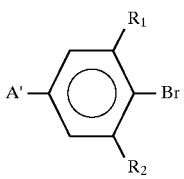

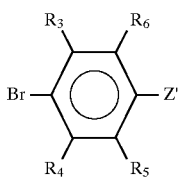

particularly by the action of magnesium turnings in anhydrous diethyl ether under reflux, then by the action of triethylborate in anhydrous diethyl ether at −70° C., then hydrolysis with a strong mineral acid such as sulfuric acid or also by bromine-metal exchange with n-butyl lithium, then treatment with trialkylborate and aqueous hydrolysis.

They can also be obtained by the action of the corresponding brominated product, supplied with the necessary protection, in the presence of n-butyllithium in tetrahydrofuran at −78° C. followed by hydrolysis with a strong mineral acid such as sulfuric acid or with water.

The products of formula II with Y as $SnBu_3$, or the products of formula III with X as $SnBu_3$ can be obtained from the corresponding brominated product III''' or III''', it being understood that regarding the product of formula III''', the OH which can be Z' is protected as described previously, particularly with tertbutyldiphenylsilyl, by the action of tributyl stannyl chloride in the presence of n-butyllithium in tetrahydrofuran at −78° C.

The compounds of formulae III, III', III'' and III''' in which Z' is Ba—CO—$NR_aR_b$ are prepared: either by the action of Hal-(CH2)$_n$—CO—$NR_aR_b$ on a compound of formula III''$_a$ or III$^a$ in the presence of a base, or by the action of H—$NR_aR_b$ in the presence of $SOCl_2$ on a compound of formula III'$_b$ or III$_b$, or by the action of H—$NR_aR_b$ in the presence of $SOCl_2$ on a compound of general formula III'$_c$ or III$_c$.

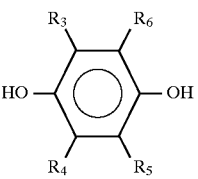

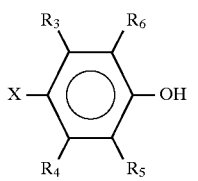

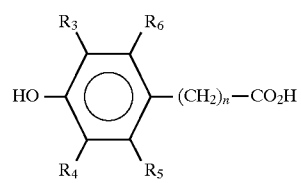

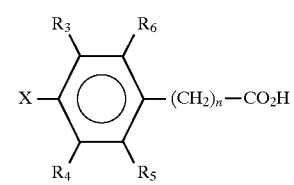

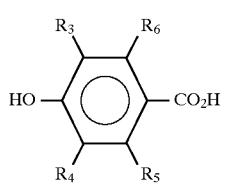

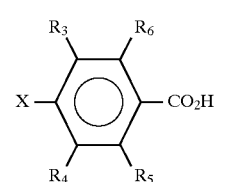

$R_1$, $R_2$, $R_3$, $R_4$, $R_5$ or $R_6$ being as defined previously, X is hydrogen, bromine or chlorine.

The products of formulae II, II', II'', II''', $III_a$, $III'_a$, $III_b$, $III'_b$, $III_c$, $III'_c$, are in general known or are accessible by applying the general principles of the chemistry of aromatic compounds known to a man skilled in the art. Among others, the following reference can be mentioned: RODD'S CHEMISTRY OF CARBON COMPOUNDS Vol. III Aromatic compounds Ed. M. F. ANSELL Elsevier Scientific Publishing Company (1981).

The products of formulae III, III', III'' and III''' in which Z' is an optionally protected hydroxyl, are also known or are accessible to a man skilled in the art.

The products of formulae III and III', III'' and III''' in which Z' is Ba—CO—$NR_aR_b$ and X is hydrogen, iodine, bromine or chlorine are also known or are accessible to a man skilled in the art.

The compounds of the formula Hal-$(CH_2)_n$CONR$_a$R$_b$ are formed by the action of HNR$_a$R$_b$ on the compound of formula Hal-$(CH_2)_n$—$CO_2H$ in the presence of a base. Hal is preferably bromine or chlorine and n is preferably equal to 1.

The products of formula I' in which Z' is an optionally protected OH are known or are accessible to a man skilled in the art who implements the coupling reactions as described in the different documents mentioned above.

The compounds of formula III in which Z' is Ba—CO—$NR_aR_b$ and X is $OSO_2CF_3$, $B(OH)_2$ or $SnBu_3$ are useful in particular for the implementation of the process of the invention. They are new and are the subject of the present invention, as are the compounds of formula I' in which Z' is Ba—CO—$NR_aR_b$.

In the following examples, there are described several preferred embodiments to illustrate the invention. However, it is to be understood that the invention is not intended to be limited to the specific embodiments.

PREPARATION 1

(4-methoxyphenyl)-boronic acid 100 ml of a solution of 10 g of p-bromoanisole in anhydrous diethyl ether were added dropwise at reflux under an inert gas atmosphere to a suspension of 1.3 g of Mg turnings in 5 ml of anhydrous diethyl ether, and the mixture was refluxed for 2 hours. The mixture was then poured into a solution of 9.02 ml of triethylborate in 60 ml of anhydrous ether cooled to −70° C. After stirring for one hour at −70° C., then for one hour at ambient temperature, the solution was poured into a mixture of 11 ml of sulfuric acid and 50 g of ice and water and stirring was carried out for one hour. The organic phase was extracted with 100 ml of a saturated aqueous solution of sodium bicarbonate and the aqueous phases were combined and reacidified with 6N hydrochloric acid, followed by extraction with ether, drying and evaporating under reduced pressure to obtain 3.9 g of the expected product.

IR Spectrum: (Nujol)

Complex absorption OH/NH region, 1609, 1573 and 1518 $cm^{-1}$

NMR: DMSO-$d_6$, 300 MHz
3.76 s $CH_3O$
6.88 (d) J=9 Hz $H_3$ and $H_5$
7.78 (d) J=9 Hz $H_2$ and $H_6$
7.86 $B(OH)_2$

PREPARATION 2

[4-(benzyloxy)-phenyl]-boronic acid

Stage A 1-bromo-4-(benzyloxy)-benzene 15.26 g of sodium hydride at 50% in oil were added at 0° C. to a solution under an inert gas atmosphere of 50 g of p-bromophenol in 320 ml of dimethylformamide and after the mixture was stirred for 30 minutes at 0° C., then 37.7 ml of benzyl bromide were added. The mixture was stirred for 2 hours 30 minutes, allowing the temperature to rise to 20° C., and then the reaction mixture was poured into ice-cooled water. The precipitate was filtered off and dried to obtain 73.35 g of the expected product with an Rf: 0.85 (thin layer chromatography, support: silica, eluant: cyclohexane/ethyl acetate 7/3).

IR Spectrum: ($CHCl_3$):

Absence of OH

Aromatic 1592, 1580 and 1488 $cm^{-1}$

Stage B

[4-(benzyloxy)-phenyl]-boronic acid 143 ml of a solution of n-butyllithium were added dropwise under an inert gas atmosphere at −78° C. to 47.08 g of the product of Stage A in 375 ml of tetrahydrofuran and after the mixture was stirred for one hour at −78° C., then 36.5 ml of triethylborate were added. The mixture was stirred overnight, allowing the temperature to rise to 20° C., and the reaction medium was hydrolyzed using a solution of ice-cooled water containing 45 ml of concentrated sulfuric acid for one hour at 20° C. The aqueous phase was extracted with ethyl acetate and the organic phases were washed with 2N sodium hydroxide. The aqueous phase was acidified to pH=1 using a solution of 1N hydrochloric acid to precipitate the boronic acid. After filtration and drying of the precipitate, 28.54 g of the expected product was obtained with a Rf=0.16 (thin layer chromatography, support: silica, eluant: cyclohexane/ethyl acetate 7/3).

IR Spectrum: (Nujol)

General absorption 3650, 3615, 3510 and 3420 $cm^{-1}$

OH/NH region

Aromatic 1605, 1570 and 1510 $cm^{-1}$

B—O 1410, 1340 $cm^{-1}$

PREPARATION 3

4-[[(1,1-dimethylethyl)-diphenylsilyl)-oxy]phenyl]-boronic acid

Stage A 1-bromo-4-[[(1,1-dimethylethyl)-diphenylsilyl]-oxy]-benzene 80.89 g of p-bromophenol, 400 ml of dimethylformamide, 31.18 g of imidazole and 125.89 g of 1,1-dimethyl-ethyl-diphenylchlorosilane were stirred for 2 hours at ambient temperature and the reaction medium was poured into 2 liters of water. Extraction was carried out with ethyl acetate, followed by decanting, drying and evaporating under reduced pressure. After crystallization from pentane, separation was carried out, followed by drying to obtain 179.24 g of the expected product with a Rf=0.53 (thin layer chromatography, support: silica, eluant: cyclohexane/AcOEt 95/5) and a melting point of 56° C.

NMR ($CDCl_3$, 300 MHz)
1.09 (s) SitBu
6.63 (m) $H_3$, $H_5$
7.17 (m) $H_2$, $H_6$
7.69 (dd) 4H for Sio2
7.4 6H for Sio2

Stage B

4-[[(1,1-dimethylethyl)-diphenylsilyl)-oxy]-phenyl]-boronic acid 60 ml of a solution of n-butyl-lithium (1.24M) in hexane were added dropwise at −78° C. under an inert gas atmosphere to a solution of 30 g of the product of stage A in 100 ml of anhydrous tetrahydrofuran, and after stirring for 30 minutes at −78° C., 9.95 ml of trimethylborate were added dropwise. After stirring for 2 hours 30 minutes, allowing the temperature of the bath to rise to 12° C., 20 ml of water were introduced dropwise and the mixture was stirred for 72 hours at ambient temperature. After evaporating the tetrahydrofuran under reduced pressure, the aqueous phase was extracted with ether, dried and concentrated under reduced pressure until 26.36 g an oil were obtained which was purified by filtration chromatography on silica with a hexane/ethyl acetate mixture 1/1 to obtain 7.73 g of the expected product in the form of the trimer and monomer.

IR ($CHCl_3$)

OSi 915 and 1255 cm$^{-1}$
B—O 1350 and 1370 cm$^{-1}$
Aromatics 1515, 1570 and 1602 cm$^{-1}$
NMR (CDCl$_3$)
1.11 tBu
6.81 and 7.88 (Ph-O)
7.3 to 7.5 (6H) and 7.72 (4H) (PhSi)

PREPARATION 4

[4-[[(1,1-dimethylethyl)-diphenylsilyl]-oxy]-phenyl]
-tributyltin 123.89 ml of a solution of sec-butyl-lithium were added dropwise at –50° C. and under an inert gas atmosphere to a solution of 50 g of the product of Stage A of Preparation 3 in 300 ml of anhydrous tetrahydrofuran, and after stirring for one hour at –50° C., 36.29 ml of tributyl tin chloride were added. After stirring for 30 minutes with the temperature having risen to ambient temperature, the reaction mixture was poured into ice-cooled water and extraction was carried out with ethyl acetate, followed by drying and evaporating to dryness under reduced pressure to obtain 38.5 g of the expected product in the form of an oil (T$_{eb}$: 230° C. under 10$^{-2}$ mbar) and with a Rf=0.36 (thin layer chromatography, support: silica, eluant: cyclohexane).
IR (CHCl$_3$)
Aromatic 1569, 1583, 1510, 1493 cm$^{-1}$

PREPARATION 5

(4-formylphenyl)-boronic acid

This product was prepared by to the method described in European Patent Application EP 0,606,065.

PREPARATION 6

[4-(hydroxymethyl)-phenyl]-boronic acid 380 mg of sodium borohydride were added to a solution of 1.5 g of (4-formylphenyl)-boronic acid in 40 ml of methanol at 0° C. under an inert atmosphere, and after stirring for 30 minutes, 200 ml of 2N hydrochloric acid were added. After evaporation under reduced pressure, the crude product was extracted with ethyl acetate and the organic phase was dried over magnesium sulfate, followed by filtration and evaporation under reduced pressure to obtain 1.5 g of the expected product with a Rf=0.15 (cyclohexane/ethyl acetate 50/50).
IR (CHCl$_3$)
Aromatics 1614, 1565, 1518 cm$^{-1}$
NMR (CDCl$_3$)
4.50 (d) C$\underline{H}_2$OH
7.92 (s) B(OH)$_2$
7.26 and 7.74 aromatic H's
5.14 (t) CH$_2$O$\underline{H}$

PREPARATION 7 methyl 4-iodo-benzoate 2.95 ml of SOCl$_2$ were added to a suspension of 10 g of 4-iodobenzoic acid in 100 ml of methanol and the reaction mixture was refluxed for 24 hours and then evaporated under reduced pressure until 10.49 g of a dry extract were obtained corresponding to the expected product with a Rf=0.55 (cyclohexane/ethyl acetate 80/20).
IR (CHCl$_3$)
CO ester 1724 cm$^{-1}$
Aromatic 1588 cm$^{-1}$

PREPARATION 8

N,N-bis-(isopropyl)-2-bromo-acetamide 12.95 ml of bromoacetyl bromide in 160 ml of ether were added dropwise under an inert gas atmosphere at –40° C. to a solution of 52 ml of diisopropylamine in 200 ml of ether and then the mixture was stirred for one hour at –40° C. After filtration of the precipitate, the filtrate was evaporated under reduced pressure and chromatographed on silica eluting with an ethyl acetate/cyclohexane mixture (9/1) to obtain 12.92 g of expected amide in the form of an oil.
NMR (CDCl$_3$)
1.26 (d) 1.39 (d) CH(C$\underline{H}_3$)$_2$
3.43 and 3.96 (m) C$\underline{H}$(CH$_3$)$_2$
3.8 (s) Br—C$\underline{H}_2$—CO
IR (CHCl$_3$)
1641, 1633 cm$^{-1}$

PREPARATION 9

2-bromo-N-(triphenylmethyl) acetamide 3.22 ml of bromoacetyl bromide were added dropwise under an inert gas atmosphere at 0° C. to 19.23 g of tritylamine in 50 ml of chloroform and then the mixture was stirred for one hour while allowing the temperature to rise to ambient temperature. After filtration of the precipitate, the organic phase was washed with 1N sodium hydroxide, dried, evaporated under reduced pressure until a residue was obtained which was purified by crystallization from ether to obtain 8.5 g of the expected amide.
NMR (CDCl$_3$)
3.9 (s) Br—C$\underline{H}_2$—CO
7.18 to 7.34 (m) aromatic H's
7.70 (s, broad) NH
IR (CHCl$_3$)
3408, 1684, 1598, 1585, 1514, 1496 cm$^{-1}$

EXAMPLE 1

4'-[[bis(isopropyl)-amino]-carbonyl]-(1,1-biphenyl)-
4-carboxylic acid

Stage A

N,N-bis-(isopropyl)-4-hydroxy-benzamide 5.92 ml of thionyl chloride and then 4 drops of dimethylformamide were added dropwise under an inert gas atmosphere to a suspension of 5.6 g of 4-hydroxybenzoic acid in 100 ml of dichloromethane and the mixture was refluxed for 50 minutes, followed by concentrating to dryness under reduced pressure. 100 ml of dichloromethane were added, and the reaction mixture was cooled using an ice-cooled bath. Then, 28.36 ml of diisopropylamine were added dropwise and the mixture stood for one hour at ambient temperature. It was washed with 2N hydrochloric acid, and the organic phase was concentrated under reduced pressure 100 ml of methanol and 10 ml of concentrated sodium hydroxide (32%) were added, and the mixture was stirred for 30 minutes followed by evaporation under reduced pressure to eliminate the methanol and to allow the product to crystallize. After filtration, 7.15 g of the expected amide were obtained.
NMR (CDCl$_3$, 250 MHz)
1.6 CH(C$\underline{H}_3$)$_2$ 3.74 CH(CH$_3$)$_2$
6.80 and 7.16 (AA'BB') aromatic H's
8.92 (s) OH
IR (Nujol)
3240, 1609, 1588 and 1520 cm$^{-1}$
Stage B 4-[[bis-(isopropyl)-amino)carbonyl]-phenyltrifluoromethanesulfonate 3.9 ml of trifluoromethanesulfonic anhydride were added dropwise under an inert gas atmosphere to a solution of 3.4 g of the product of Stage A in 30 ml of pyridine cooled to 0° C. The mixture was stirred for one hour at this temperature and the mixture was poured into about 150 ml of ice-cooled water. The crystallized product was filtered off then dried to obtain 5.07 g of the expected trifluoromethanesulfonate in the form of a white power.
IR (CHCl$_3$)
1427 and 1140 cm$^{-1}$ (OTf)
1627 cm$^{-1}$ (CO)
1603 and 1502 cm$^{-1}$ (aromatics)
Stage C N,N-bis-(isopropyl)-4'-methyl-(1,1'-biphenyl)-4-carboxamide 76 mg of palladium tetrakis triphenylphosphine, 2.6 ml of a solution of 2M sodium carbonate, 8 ml of 99% ethanol, 298 mg of 4-methylphenylboronic acid (Commercial: LANCASTER) and 170 mg of anhydrous lithium chloride were added successively under an inert gas atmosphere to a solution of 700 mg of the product of stage B in 18 ml of toluene, and the mixture was heated to 95° C. for 3 hours. 20 ml of distilled water were added and the organic solution was washed with a saturated solution of ammonium chloride, dried over magnesium sulfate and evaporated under reduced pressure. A brown oil was obtained which crystallized and was purified by chromatography with an ethyl acetate-cyclohexane mixture (1-1) as eluant in order to obtain 594 mg of the expected product.
NMR (CDCl$_3$, 250 MHz)
1.35 (broad m) CH(CH$_3$)$_2$
3.71 (broad m) CH(CH$_3$)$_2$
2.4 (s) CH$_3$Ph
7.25 and 7.59 (AA'BB') Ar
7.37 and 7.49 (AA'BB') Ar
Stage D 4'-[[bis-(isopropyl)amino]-carbonyl]-(1,1'-biphenyl)-4-carboxylic acid 466 mg of potassium permanganate were added to a solution of 293 mg of the biphenyl of stage C in 1 ml of pyridine and 4 ml of an aqueous solution of 20% KOH at 95° C.–100° C. and the mixture was held at this temperature for 8 hours. After cooling, and elimination by filtration of a light precipitate, the filtrate was acidified with a 2N hydrochloric acid solution. The precipitate was washed with water then dried to obtain 234 mg of the expected product.
NMR (DMSO)
1.08 to 1.6 CH(CH$_3$)$_2$
3.76 (broad m) CH(CH$_3$)$_2$
7.40 and 7.78 Ar
7.83 and 8.04 Ar
13.02 COOH
IR (Nujol)
1688, 1624, 1606, 1572 cm$^{-1}$

EXAMPLE 2

4'-[2-[bis-(isopropyl)amino]-2-oxoethoxy)-(1,1'-biphenyl)-4-carboxylic acid

Stage A

N,N-bis-(isopropyl)-2-(4-iodophenoxy)-acetamide 1.38 g of 50% sodium hydride suspended in oil were added under an inert gas atmosphere to a solution of 5.2 g of paraiodophenol in 30 ml of tetrahydrofuran and after stirring at 0° C., then 6.30 g of N,N-bis-(isopropyl)-2-bromo-acetamide (Preparation 8) were added. After stirring for 2 hours while allowing the temperature to rise to 20° C., the reaction medium was poured into ice-cooled water and filtration was carried out followed by drying to obtain 9.3 g of the expected product.
NMR (CDCl$_3$, 250 MHz)
1.20 (d) and 1.39 (d): CH(CH$_3$)$_2$
3.42 (m) and 4.03 (m): CH(CH$_3$)$_2$
4.58 (s): CO—CH$_2$—O
6.73 and 7.55: Ar
IR (CHCl$_3$)
Absence of OH
(CO) 1638 cm$^{-1}$
Aromatic 1586, 1576 and 1486 cm$^{-1}$
Stage B N,N-bis-(isopropyl)-2-[[4'-formyl-(1,1'-biphenyl)-4-yl]oxy]-acetamide 0.5 g of palladium tetrakis triphenylphosphine, 3.0 g of tripotassium phosphate 1-hydrate, 1.43 g of 4-formylphenyl-boronic acid (Preparation 5) were added successively under an inert gas atmosphere to a solution of 3.14 g of the product of stage A in 40 ml of dioxane and the mixture was refluxed for 2 hours. Then, the reaction mixture was poured into ice-cooled water and the organic phase was dried over magnesium sulfate, then concentrated under reduced pressure to obtain 3.94 g of product which was purified by chromatography, eluting with an ethyl acetate/cyclohexane mixture (2/8) to obtain 833 mg of the expected product.
NMR (CDCl$_3$, 250 MHz)
1.24 (d) and 1.43 (d) CH(CH$_3$)$_2$
3.46 (m) and 4.09 (m) CH(CH$_3$)$_2$
4.69 (s) OCH$_2$CO
7.06 (d) and 7.59 (d) aromatic H (Ar—O)
7.71 (d) and 7.93 (d) aromatic H (Ar—CHO)
10.04 (s) CHO
Stage C 4'-[2-[bis-(isopropyl)-amino]-2-oxoethoxy)-(1,1'-biphenyl)-4-carboxylic acid.

0.85 ml of Jones' reagent were introduced under an inert gas atmosphere into a solution of 741 mg of the product of stage B in 10 ml of acetone and the mixture was stirred for 7 hours. The precipitate formed was filtered off and dried to obtain 620 mg of the expected product with a Rf=0.5 (dichloromethane/methanol 9/1).
NMR (CDCl$_3$, 250 MHz)
1.18 (d) and 1.31 (d) CH(CH$_3$)$_2$
3.48 (m) and 3.99 (m) CH(CH$_3$)$_2$
4.77 (s) OCH$_2$CO
7.02 (d) and 7.68 (d) aromatic H (Ar—O)
7.75 (d) and 7.99 (d) aromatic H (Ar—COOH)
12.85 (broadened) CO$_2$H
IR (CHCl$_3$)

Absorption OH/NH region
1712 cm$^{-1}$ (CO)
1622 cm$^{-1}$ (CO)+
1606, 1587, 1530 and 1498 cm$^{-1}$ (aromatics)

Microanalysis % calculated: C 70.96 H 7.09 H 3.94 % found: C 70.9 H 7.2 H 3.9

EXAMPLE 3

4'-[2-[bis(isopropyl)amino]-2-oxoethoxy]-3', 5'-bis(isopropyl)-(1,1'-biphenyl)-4-carboxylic acid Using the procedure of Example 2, Stages A and B, 2 g of 2', 6'-diisopropyl-4-bromo-phenol were reacted and the oxidation of the formyl group (Stage C) was carried out with Ag$_2$O as described in Example 10, Stage B to obtain 54 mg of expected product with a Rf=0.23 (dichloromethane-methanol 9-1)).

IR (CHCl$_3$)
presence of acid judged according to the OH region carbonyl 1728, 1691, 1655, 1639 cm$^{-1}$
aromatic 1609, 1565, 1515 cm$^{-1}$
NMR (CDCl$_3$, 300 MHz)
1.30 (d) 1.49 (d) CH(CH$_3$)$_2$
3.54 (bm) and 4.10 (bm) CH(CH$_3$)$_2$
3.39 (m) Ph—CH(CH$_3$)$_2$
4.45 (s) O—CH$_2$—CO
7.34 (s) aromatic H'$_2$'s, H'$_6$'s (Ar—O)
7.64 (d) 8.05 (d) aromatic H's (Ar—COOH)

EXAMPLE 4

4'-[2-[bis-(isopropyl)-amino]-2-oxoethoxy]-3'-fluoro-5'-nitro-(1,1'-biphenyl)-4-carboxylic acid Using the procedure of Example 2, Stages A, B and C, 5 g of 2-fluoro-4-bromo-6-nitro-phenol were reacted to obtain 1.8 g of the expected product with a melting point of 202° C.

IR (CHCl$_3$)
presence of acid judged according to the OH region carbonyl 1703, 1648 cm$^{-1}$
aromatic 1611, 1569, 1543, 1518 cm$^{-1}$
NMR (CDCl$_1$, 250 MHz)
1.16 (d) 1.27 (d) CH(CH$_3$)$_2$
3.48 (bm) and 3.77 (bm) CH(CH$_3$)$_2$
5.05 (s) and 5.06 (s) O—CH$_2$—CO
7.95 to 8.10 aromatic H'$_2$'s, H'$_6$'s (Ar—O)
7.88 (m) 8.03 (m) (AA'BB') aromatic H's (Ar—COOH)

EXAMPLE 5

4'-[2-oxo-2-([tribenzyl)-amino]-ethoxy]-(1,1'-biphenyl)-4-carboxylic acid

Stage A 2-(4-bromophenoxy)-N-(tribenzyl)-acetamide

Using the procedures of Example 2, Stage A, 560 mg of p-bromophenol and 1.3 g of 2-bromo-N-(tribenzyl) acetamide (preparation 9) were reacted to obtain 1.81 g of expected product.

IR (CHCl$_3$)
Absence of OH
=C—NH 3420 cm$^{-1}$
C=O 1689 cm$^{-1}$
aromatic amide: 1592, 1585, 1510, and 1490 cm$^{-1}$
NMR (CDCl$_3$) 300 MHz
4.47 (s) O—CH$_2$—CO
6.79 and 7.41 (AA'BB'): aromatic 4H's
7.15 to 7.32 trityl
7.74 (bs) NHCO Stage B 4'[[4'-formyl(1,11'-biphenyl)-4-yl]oxy])-N-(tribenzyl)-acetamide Using the procedure of Example 2, Stage B (adding 1.1 equivalent of potassium bromide), 1.5 g of the product of Stage A and 525 mg of boronic acid were reacted to obtain 160 mg of the pure expected product.

NMR (CDCl$_3$) 300 MHz
4.56 (s) O—CH$_2$—CO
7.71 and 7.95 (AA'BB'): aromatic 4H's (Ar—CHO)
7.03 and 7.61 (AA'BB'): aromatic 4H's (Ar—O)
7.20 to 7.33 (m) trityl
7.83 (bs) NHCO
10.05 CHO
4.56 (s) O—CH$_2$—CO Stage C 4'-[2-oxo-2-([tribenzyl)-amino](ethoxy]-(1,1'-biphenyl)-4-carboxylic acid Using the procedure of Example 3, Stage C, 270 mg of the product of Stage B were reacted to obtain, 60 mg of the expected product with a Rf=0.43 (dichloromethane/methanol 98/02).

IR (CHCl$_3$)
General absorption OH/NH
C=O 1692, 1672 cm$^{-1}$
aromatic+amide II: 1608, 1585, 1525, and 1492 cm$^{-1}$
NMR (CDCl$_3$) 300 MHz
4.76 (s) O—CH$_2$—CO
6.96 and 7.65 (AA'BB'): aromatic 4H's Ar—O
7.75 and 7.99 (AA'BB'): aromatic 4H's ArCOOH
7.18 to 7.35 (m) trityl
8.72 (s) NHCO
12.95 CO$_2$H

EXAMPLE 6

3'-fluoro-5'-nitro-4'-[2-oxo-2-[(tribenzyl)-amino]-ethoxy]-(1,1'-biphenyl)-4-carboxylic acid Using the procedure of Example 5, Stages A and B, 0.638 g of 2-fluoro-4-bromo-6-nitro-phenol were reacted and carrying out the oxidation of the formyl group (Stage C) with NaClO/H$_2$NSO$_3$H as described in Example 9, Stage C, 43 mg of expected product were obtained after crystallization from chloroform with a melting point of 236°–7° C.

IR (CHCl$_3$)
NH 3410 cm$^{-1}$
C=O 1730, 1695 cm$^{-1}$
amide II, aromatic, NO$_2$ 1613, 1583, 1566, 1545, 1516 and 1492 cm$^{-1}$
MR (CDCl$_3$) 300 MHz
4.78 (d) O—CH$_2$—CO
8.01 (m): H'$_2$ Ar—O
7.69 (dd): H'$_6$ Ar—O
7.68 and 8.23 (AA'BB'): aromatic 4H's ArCOOH
7.31 (m) trityl
8.06 (bs) NHCO
12.95 CO$_{2H}$

EXAMPLE 7

4'-[2-[bis-(isopropyl)amino]-2-oxoethoxy]-2', 3'-dicyano -(1,1'-biphenyl)-4-carboxylic acid Stage A

N,N-bis-(isopropyl)-2-(2,3-dicyano-4-hydroxy-phenoxy)-acetamide 960 mg of sodium hydride (50% in oil) were added to a solution of 1.6 g of 2,3-dicyano-4-hydroxy-phenol in 100 ml of dimethylformamide, and after stirring for 30 minutes at ambient temperature, then 2.3 g of N,N-bis(isopropyl)-2-bromoacetamide (preparation 8) were added. After stirring for 48 hours, the solvent was evaporated under reduced pressure and 200 ml of 2N hydrochloric acid were added. Extraction was carried out with ethyl acetate and the organic phase was dried over magnesium sulfate, filtered and evaporated under reduced pressure. The residue was chromatographed, eluting with a cyclohexane-ethyl acetate mixture (50/50), then with pure ethyl acetate, and finally an ethyl acetate-methanol mixture (98/2) to obtain 1.8 g of the expected product is obtained which was used as is for the following stage.

Stage B

[4-[2-[bis-(isopropyl)-amino]-2-oxoethoxy]-2,3-dicyanophenyl]trifluoromethanesulfonate.

0.58 ml of ethyl diisopropylamine and 0.59 ml of trifluoromethanesulfonic anhydride were added to a solution of 900 mg of the product of Stage A in 50 ml of acetonitrile and the reaction medium was refluxed for one hour. Then, the solvent was evaporated under reduced pressure and the crude product obtained was chromatographed on silica, eluting with a cyclohexane-ethyl acetate mixture (50-50) to obtain 600 mg of the expected product.

IR (CHCl$_3$)
nitrile 2245 cm$^{-1}$
carbonyl 1656, 1644 cm$^{-1}$
aromatic 1594 cm$^{-1}$
NMR (CDCl$_3$, 250 MHz)
1.28 (d) 1.38 (d) CH(C$\underline{H}_3$)$_2$
3.49 (m) 3.94 (m) C$\underline{H}$(CH$_3$)$_2$
4.90 (s) O—C$\underline{H}_2$—CO
7.38 (d) 7.62 (d) aromatic H's Stage C

N,N-bis-(isopropyl)-2-[[2,3-dicyano-4'-(hydroxy-methyl)-(1,1'-biphenyl)-4-yl]-oxy]-acetamide 1.1 g of the product of Stage B, 875 mg of tripotassium phosphate monohydrate, 330 mg of potassium bromide, 75 mg of palladium tetrakis, 425 mg of boronic acid (Preparation 6) and 50 ml of dioxane were mixed together under an inert gas atmosphere and the mixture was stirred for 16 hours at reflux. After evaporation under reduced pressure, the residue was chromatographed on silica, eluting with a 50-50 mixture of cyclohexane-ethyl acetate, then ethyl acetate to obtain 140 mg of the expected product.

IR (CHCl$_3$)
nitrile 2240 cm$^{-1}$
alcohol 3612 cm$^{-1}$
carbonyl 1655, 1642 cm$^{-1}$
aromatic 1595, 1562 cm$^{-1}$
NMR (CDCl$_3$, 250 MHz)
1.28–1.39 (d) CH(C$\underline{H}_3$)$_2$
1.84 OH
3.48–4.08 (m) C$\underline{H}$(CH$_3$)$_2$
4.88 (s) CO—C$\underline{H}_2$—O
7.39–7.64 (d) aromatic H's Ar—O
7.5 (s) aromatic H's Ar—CH$_2$OH
4.78 (d) C$\underline{H}_2$—OH Stage D

4'-[2-[bis-(isopropyl)-amino]-2-oxoethoxy]-2', 3'-dicyano -(1,1-biphenyl)-4-carboxylic acid 30 mg of the product of Stage C, 0.1 ml of Jones' reagent and 10 ml of acetone were mixed together under an inert gas atmosphere for 15 minutes and then the mixture was poured into water. The solid was filtered, dried and then crystallized from 2 ml of ethyl acetate to obtain 12 mg of the expected product with a Rf=0.2 (in ethyl acetate).

IR (CHCl$_3$)
nitrile 2240 cm$^{-1}$
carbonyl 1700, 1656 cm$^{-1}$
aromatic 1612, 1595, 1558, 1515 cm$^{-1}$
NMR (CDCl$_3$, 250 MHz)
1.25 (d) 1.39 (d) CH(C$\underline{H}_3$)$_2$
3.48 (m) 4.07 (m) C$\underline{H}$(CH$_3$)$_2$
4.93 (bs) O—C$\underline{H}_2$—CO
7.44 (d) 7.68 (d) aromatic H's (Ar—O)
7.62 (d) 8.22 (d) aromatic H's (Ar—COOH)

EXAMPLE 8

4-[4-[2-[bis-(isopropyl)-amino]-2-oxoethoxy]-1-naphthalenyl]-benzoic acid

Using the procedure of Example 7, Stages A, B, C and D, 3.2 g of 1,4-dihydroxy naphthalene were reacted to obtain 20 mg of the expected product with a Rf=0.14 (cyclohexane-ethyl acetate 50-50).

IR (CHCl$_3$)
carbonyl 1725, 1692, 1653, 1638 cm$^{-1}$
aromatic 1609, 1596, 1585, 1564, 1510, 1507 cm$^{-1}$
NMR (CDCl$_3$, 250 MHz)
1.24 (d) 1.47 (d) CH(C$\underline{H}_3$)$_2$
3.48 (m) 4.25 (m) C$\underline{H}$(CH$_3$)$_2$
4.87 (s) O—C$\underline{H}_2$—CO
6.97 (d) J=8
7.34 (d) J=8
7.84 (m) aromatic H of the naphthalene
8.41 (m)
7.50 (m)
7.59–8.22 aromatic H's Ar—CO$_2$H

EXAMPLE 9

4'-[2-[bis-(isopropyl)]-2-oxoethyl)-(1,1'-biphenyl)-4-carboxylic acid

Stage A

N,N-bis-(isopropyl)-4-bromo-benzeneacetamide 4.21 g of 1-ethyl 3-(3-dimethylamino-propyl)-carbodiimide (EDAC) and 3.08 ml of diisopropylamine were added to a solution of 4.3 g of 4-bromo-benzeneacetic acid (BrPhCH$_2$COOH) in 15 ml of dichloromethane and the mixture was stirred for 10 minutes at ambient temperature. After evaporation under reduced pressure, the crude product was chromatographed on silica, eluting with an ethyl acetate/cyclohexane mixture (2/8) to obtain 3.7 g of product in the form of an oil with a Rf=0.21 ethyl acetate/cyclohexane 2/8).

Stage B

N,N-bis-(isopropyl)-4'-formyl-(1,1'-biphenyl)-4-acetamide

A mixture of 3 g of the product of Stage A, 1.66 g of boronic acid (Preparation 5), 3.5 g of monohydrated potassium phosphate, 1.32 g of potassium bromide and 300 mg of Pd(PPh3)4 (palladium tetrakis) in 50 ml of dioxane was refluxed for 12 hours. After pouring the reaction medium into a water-ice mixture, and carrying out extraction with ethyl acetate, the organic phase was dried, filtered and evaporated under reduced pressure. The crude product was purified by chromatography, eluting with a cyclohexane/ethyl acetate mixture (85/15) to obtain 1.95 g of the expected product with a Rf=0.05 (cyclohexane/ethyl acetate 85/15).

IR (CHCl$_3$)
aldehyde and amide 1702, 1632 cm$^{-1}$
aromatics 1606, 1579, 1560, 1524, 1490 cm$^{-1}$ Stage C 4'-[2-[bis-(isopropyl)-amino]-2-oxoethyl)-(1,1'-biphenyl) -4-carboxylic acid 418 mg of sodium chlorite monohydrate in 1.5 ml of water and 497 mg of aminosulfonic acid were added to a solution of 600 mg of the product of Stage B in 5 ml of tetrahydrofuran, and the mixture was stirred for 10 minutes at ambient temperature. Ethyl acetate was added and the mixture was extracted with 2N sodium hydroxide. The aqueous phase was acidified with 2N hydrochloric acid, extracted with ethyl acetate, dried and then evaporated under reduced pressure to provide the expected crude product which was chromatographed on silica, eluting with an acetonitrile/water mixture (8/2) to obtain 40 mg of the expected product.

NMR (DMSO)
1.02 (d) and 1.32 (d) CH(C$\underline{H}_3$)$_2$
3.42 (m) and 4.05 (m) C$\underline{H}$(CH$_3$)$_2$
3.71 (s) C$\underline{H}_2$CO
7.34 (d) 7.69 (d) aromatics
7.80 (d) 8.01 (d) aromatics
12.86 (broadened) mobile H's
IR (Nujol)
CO 1708 cm$^{-1}$
aromatics, amide 1608, 1584, 1562, 1530 and 1499 cm$^{-1}$

EXAMPLE 10

4'-[2-[bis-[isopropyl]-amino]-1-methyl-2-oxoethyl]-(1,1'-biphenyl)-4-carboxylic acid Stage A N,N-bis-(isopropyl)-4'-formyl-α-methyl-(1,1'-biphenyl)-4-acetamide 1.29 g of the product of Example 9, Stage B in 0.42 ml of ethylene glycol, 35 mg of p-toluene sulfonic acid and 40 ml of toluene were refluxed for 3 hours and after 0.42 ml of ethylene glycol were added, the mixture was refluxed for another 2 hours. The reaction medium was then poured into a saturated solution of sodium bicarbonate, then extraction was carried out with dichloromethane. The extracts were dried, then evaporated under reduced pressure to obtain 1.23 g of protected product. After dissolution of this product in 20 ml of tetrahydrofuran, 1.2 equivalents of lithium diisopropylamine (prepared from 0.54 ml of diisopropylamine and 3.3 ml of n-butyllithium in hexane) were added at −78° C., and the mixture was stirred for one hour at this temperature and 0.31 ml of methyl iodide were added. After stirring for 30 minutes at ambient temperature, the mixture was poured over ice and extraction was carried out with ethyl acetate. The organic phase was dried, evaporated under reduced pressure and chromatographed on silica, eluting with a cyclohexane/ethyl acetate mixture (7/3) to obtain 922 mg of intermediate ketal.

A mixture of 460 mg of the ketal obtained previously, 1.6 ml of 6N hydrochloric acid and 5 ml of ethanol was refluxed for 12 hours and then poured over ice and extracted with ethyl acetate. The organic phase was dried and evaporated under reduced pressure to obtain 393 mg of the expected aldehyde, used as is for the following stage.

Stage B

4'-[2-[bis-[isopropyl]-amino]-1-methyl-2-oxoethyl]-(1,1'-biphenyl)-4-carboxylic acid 18.04 ml of 1N sodium hydroxide and 3.14 g of Ag$_2$O were added to a solution of 380 mg of the product of Stage A in 8 ml of tetrahydrofuran and the mixture was stirred for 24 hours at ambient temperature. After adding 6N hydrochloric acid, extraction was carried out with ethyl acetate to obtain 380 mg of the expected product which is recrystallized from isopropanol to obtain a Rf=0.11 (ethyl acetate/cyclohexane 1/1).

NMR (DMSO)
0.59 (d) CH—C$\underline{H}_3$
1.1 (d) and 1.26 (d) CH(C$\underline{H}_3$)$_2$
1.28 (d) and 1.35 (d)
3.33 (masked, m) and 4.07 (m) C$\underline{H}$(CH$_3$)$_2$ and C$\underline{H}$—CH$_3$
7.36 (d) 7.71 (d) aromatics
7.79 (d) 8.00 (d) aromatics
12.97 (broadened) mobile H's
IR (Nujol)
CO 1716 cm$^{-1}$
aromatics, amide 1606, 1580 and 1492 cm$^{-1}$

EXAMPLE 11

4'-[2-[(isopropyl)-amino)-2-oxoethoxy]-2'-ethyl-(1,1'-biphenyl)-4-carboxylic acid Stage A
Product A: 2-ethyl-4-(benzyloxy)-phenol.
Product B: 3-ethyl-4-(benzyloxy)-phenol.

1) 7.5 g of imidazole and 9.3 ml of diphenyl terbutyl chlorosilane were added under an inert gas atmosphere to a solution of 5 g of 2-ethyl-3-hydroxyphenol in 100 ml of dimethylformamide and the mixture was stirred for 48 hours at ambient temperature. The solvent was evaporated under reduced pressure and the crude product was taken up in water. Extraction was carried out with ethyl acetate and the extracts were dried over magnesium sulfate and evaporated under reduced pressure. The residue was purified by chromatography on silica, eluting with a cyclohexane/ethyl acetate mixture (95/5) to obtain 10 g of a mixture of two crude products with a Rf=0.12 cyclohexane/ethyl acetate 98/2).

2) 1.4 g of sodium hydride (50% in oil) and then 3.6 ml of benzyl bromide were added to a solution of the mixture of the preceding products in 200 ml of dimethylformamide and the mixture was stirred for 24 hours at ambient temperature. After evaporating the solvent under reduced pressure, the crude product was taken up in water, extraction is carried out with ethyl acetate. The organic phase was dried over magnesium sulfate, filtered and then evaporated under reduced pressure to obtain 12 g of a mixture of two crude products.

3) The mixture of the preceding products was mixed at ambient temperature over one hour with 40 ml of tetrabutyl ammonium fluoride and 300 ml of tetrahydrofuran and then the solvent was evaporated under reduced pressure. After chromatography on silica, eluant: cyclohexane-ethyl acetate (95-5), 900 mg of product A and 1.9 g of product B were obtained.

Product A 2-ethyl-4-(benzyloxy)-phenol with a Rf=0.45
(cyclohexane-ethyl acetate 80-20)

IR (CHCl$_3$)
3605 cm$^{-1}$ phenol
1600, 1506 cm$^{-1}$ aromatics
NMR (250 MHz, CDCl$_3$)
7.25 7.47 (m) aromatic H of benzyl
5.00 (s) CH$_2$ of the benzyl
6.68 (m) 2H aromatic H's of the phenol
6.80 (bs) 1H aromatic H's of the phenol
2.60 (q) CH$_2$CH$_3$
1.25 (t) CH$_2$CH$_3$
4.37 (s) OH Product B 3-ethyl-4-(benzyloxy)-phenol with a Rf=0.40
(cyclohexane-ethyl acetate 80-20)

IR (CHCl$_3$)
3603 cm$^{-1}$ phenol
1599, 1502 cm$^{-1}$ aromatics
NMR (250 MHz, CDCl$_3$)
7.25 7.47 (m) aromatic H of benzyl
5.01 (s) CH$_2$ of the benzyl
6.59 (dd), 6.69 (d) 6.77 (d) aromatic H's of the phenol
2.66 (q) CH$_2$CH$_3$
1.20 (t) CH$_2$CH$_3$
4.42 (s) OH Stage B 2'-ethyl-4'-(benzyloxy)-(1,1'-biphenyl)-4-carboxaldehyde 1) Formation of the trifluoromethanesulfonate 1.64 g of diterbutyl methyl pyridine and 1.3 ml of trifluoromethanesulfonic anhydride were added under an inert gas atmosphere to 900 mg of product A of Stage A in solution in 50 ml of dichloromethane and the mixture was stirred for 3 hours at ambient temperature. After washing with water, the organic phase was dried over magnesium sulfate, filtered and then evaporated to dryness under reduced pressure. The residue was chromatographed on silica (cyclohexane/ethyl acetate 90/10) to obtain 1.4 g of the trifluoromethanesulfonate which was used in the coupling reaction. It has a Rf=0.5 (cyclohexane/ethyl acetate 90/10).

2) Coupling 1.4 g of the preceding trifluoromethanesulfonate, 150 ml of dioxane, 2 g of tripotassium phosphate monohydrate, 920 mg of potassium bromide, 200 mg of palladium tetrakis and 1040 mg of boronic acid were mixed together under an inert gas atmosphere, and the mixture was taken to refluxed for 4 hours. After evaporation under reduced pressure, the crude product obtained was chromatographed on silica, eluting with a cyclohexane-ethyl acetate mixture (95-5) to obtain 830 mg of the expected product with a Rf=0.5 (cyclohexane/ethyl acetate 80-20).

IR (CHCl$_3$)
carbonyl 1701 cm$^{-1}$
aromatics 1606, 1573, 1563, 1516, 1487 cm$^{-1}$
NMR (300 MHz, CDCl$_3$)
7.2 to 7.5 (m) aromatic H of the benzyl
5.12 (s) O—CH$_2$Ph
6.97 (d) H'$_3$
6.88 (dd) H'$_5$
7.07 (d) H'$_6$
2.58 (q) CH$_2$CH$_3$
1.1 (t) CH$_2$CH$_3$
7.46, 7.91 aromatic H's (Ar—CHO)
10.24 (s) CHO Stage C 2'-ethyl-4'-(benzyloxy)-(1,1'-biphenyl)-4-carboxylic acid 0.3 ml of Jones' reagent were added under an inert gas atmosphere to a solution of 400 mg of the product of Stage B in 20 ml of acetone and the mixture was stirred for 30 minutes at ambient temperature. The medium was then taken up in a mixture of 100 ml of water and 100 ml of ethyl acetate and the organic phase was dried over magnesium sulfate, filtered and evaporated under reduced pressure until a crude product was obtained which was crystallized from 20 ml of a 50/50 mixture of ether/pentane to obtain 400 mg of the expected product with a Rf=0.1 (cyclohexane/ethyl acetate 80 20).

IR (CHCl$_3$)
carbonyl 1676 cm$^{-1}$
aromatics 1610, 1566, 1518, 1496 cm$^{-1}$ Stage D 2'-ethyl-4'-hydroxy-(1,1'-biphenyl)-4-carboxylic acid 400 mg of the product of Stage C were added to 100 mg of palladium on charcoal in 50 ml of ethyl acetate. After 24 hours of stirring at ambient temperature under a hydrogen atmosphere, the reaction medium was filtered and evaporated under reduced pressure until a crude product was obtained which was purified by chromatography on silica, eluting with a CH$_2$Cl$_2$/AcOH mixture (997/003) to obtain 110 mg of expected product with a Rf=0.1 CH$_2$Cl$_2$/MeOH 95/5).

IR (CHCl$_3$)
hydroxyl 3600 cm$^{-1}$
carbonyl 1723, 1693 cm$^{-1}$
aromatics 1611, 1582, 1566, 1514 cm$^{-1}$ Stage E 4'-(2-[bis-(isopropyl)-amino)-2-oxoethoxy]-2'-ethyl-(1,1'-biphenyl)-4-carboxylic acid Using the procedure of Example 2, Stage A, 70 mg of the product of Stage D were reacted to obtain 40 mg of the expected product with a Rf=0.18 (cyclohexane/ethyl acetate 80/20).

IR (CHCl$_3$)
hydroxyl 3500 cm$^{-1}$
carbonyl 1734, 1720, 1692, 1654, 1637 cm$^{-1}$
aromatics 1575, 1564, 1518, 1487 cm$^{-1}$
NMR (300 MHz, CDCl$_3$)
1.25 (d) 1.44 (d) CH(CH$_3$)$_2$
3.47 (m) 4.11 (m) CH(CH$_3$)$_2$
4.68 (s) O—CH$_2$—CO
6.83 (dd) H'$_3$
7.12 (d) H'$_5$
6.93 (d) H'$_6$
2.57 (q) CH$_2$CH$_3$
1.09 (t) CH$_2$CH$_3$
7.39 8.14 aromatic H's (Ph—COOH)
12.96 (s) COOH

EXAMPLE 12

4'-[2-[bis-(isopropyl)-amino)-2-oxoethoxy]-3'-ethyl-(1,1'-biphenyl)-4-carboxylic acid Using the procedure of Example 11, Stages B, C, D and E, 1.9 g of product B prepared in Stage A of Example 11 were reacted to obtain 40 mg of the expected product with a Rf=0.5 (ethanol).

IR (CHCl$_3$)
carbonyl 1690, 1636 cm$^{-1}$
aromatics 1607, 1565, 1520, 1493 cm$^{-1}$
NMR (300 MHz, CDCl$_3$)
1.24 (d) 1.42 (d) CH (C$\underline{H}_3$)$_2$
3.46 (m) 4.19 (m) C$\underline{H}$(CH$_3$)$_2$
4.70 (s) O—C$\underline{H}_2$—CO
6.97 (d J=8.5) H'$_5$
7.44 (m) H'$_2$, H'$_6$
2.75 (s) C$\underline{H}_2$CH$_3$
1.24 (m) CH$_2$C$\underline{H}_3$
7.65 8.14 aromatic H's (Ph—COOH)
Microanalysis
calculated: % C 72.04 % H 7.62 % N 3.65 % O 16.69
found: % C 71.7 % H 7.7 % N 3.3

EXAMPLE 13

4'-[2-[bis-(isopropyl)-amino]-2-oxoethoxy]-2-chloro-(1,1'-biphenyl)-4-carboxylic acid Stage A methyl 3-chloro-4-[[(trifluoromethyl)sulfonyl]oxy]-benzoate A mixture of 3 g of methyl 3-chloro-4-hydroxybenzoate, 5.3 ml of trifluoromethanesulfonic anhydride and 30 ml of pyridine was stirred for 6 hours under an inert gas atmosphere at 0° C. and then was poured into ice-cooled water. After extraction with ethyl acetate, and drying of the organic phase over magnesium sulfate, concentration was carried out under reduced pressure to obtain 6.84 g of the expected product.

NMR (DMSO 300 MHz)
3.90 (s) CO$_2$C$\underline{H}_3$
8.09 (dd) H$_6$
7.83 (d) H$_5$
8.23 (d) H$_2$
IR (Nujol)
1740 cm$^{-1}$ (CO)
1660 cm$^{-1}$ (CO)
1640, 1628, 1603 (sh), 1546 and 1492 cm$^{-1}$ (aromatics)

Stage B methyl 2-chloro-4'-(benzyloxy)-(1,1'-biphenyl)-4-carboxylate

A mixture of 1.58 g of the trifluoromethane-sulfonate prepared previously, 1.13 g of (4-(benzyloxy)-phenyl)-boronic acid (Preparation 2), 0.29 g of palladium tetrakis (triphenyl-phosphine,) 1.72 g of tripotassium phosphate monohydrate, 0.65 g of potassium bromide and 15 ml of dioxane was refluxed for 3 hours and then was poured into ice-cooled water. After extraction with ethyl acetate, and drying of the organic phase over magnesium sulfate, concentration was carried out under reduced pressure to obtain 1.83 g of a brown oil which was purified by chromatography on silica, eluting with a 98/2 mixture of cyclohexane/ethyl acetate to obtain 0.956 g of the expected product.

NMR (DMSO, 300 MHz)
3.95 (s) CO$_2$C$\underline{H}_3$
7.95 (dd) H$_5$
7.3, 7.5 (m) arom. 6H: H$_6$+5H of the benzyl
8.13 (d) H$_3$
7.04 and 7.41 (AA'BB') aromatic H (Ar—O)
5.12 (s) C$\underline{H}_2$ of the benzyl Stage C methyl 2-chloro-4'-hydroxy-(1,1'-biphenyl)-4-carboxylate The mixture of 286 mg of the product of Stage B, 91 mg of 9.5% palladium on charcoal and 20 ml of ethyl acetate was placed under a hydrogen atmosphere and the mixture was stirred at 20° C. for 24 hours. After filtration and concentration under reduced pressure, 211 mg of the expected product were obtained.

NMR (CDCl$_3$, 200 MHz)
3.9 (s) CO$_2$C$\underline{H}_3$
7.85 (d) H$_5$
7.75 (m) 3H H$_6$, H'$_2$, H'$_6$
8.05 (s) H$_3$
6.9(d) 2H H'$_3$, H'$_5$ Stage D 4'-[2-[bis-(isopropyl)-amino]-2-oxoethoxy]-2-chloro-(1,1'-biphenyl)-4-carboxylic acid 1) Alkylation 48 mg of sodium hydride (as a 50% suspension in oil) and 220 mg of N,N-bis-(isopropyl)-2-bromo-acetamide (preparation 8) were added under an inert gas atmosphere at 0° C. to a mixture of 260 mg of the product of Stage C in 5 ml of tetrahydrofuran and the mixture was stirred for 3 hours 30 minutes while allowing the temperature to rise to 20° C. The reaction medium was poured into 50 ml of ice-cooled water and extraction was carried out with ethyl acetate. The organic phases were dried over magnesium sulfate and after concentration under reduced, pressure 385 mg of an oil were isolated which was used as is in the saponification.

2) Saponification

A mixture of 203 mg of the oil obtained in the preceding stage, 1 ml of 2N sodium hydroxide and 5 ml of tetrahydrofuran was stirred at reflux for 24 hours and the reaction mixture was poured into 50 ml of water. Extraction was carried out with ethyl acetate and the organic phases were washed with 2N hydrochloric acid. The organic phases were dried over magnesium sulfate and concentrated under reduced pressure to obtain 169 mg of the expected product with a Rf=0.39 (dichloromethane/methanol 9/1).

NMR (CDCl$_3$, 250 MHz)
1.23 1.42 CH CH(C$\underline{H}_3$)$_2$
3.45 4.05 C$\underline{H}$(CH$_3$)$_2$
4.64 (s) OC$\underline{H}_2$ CO
6.95 7.28 aromatic H's (Ar—O)
8.16 (bs) H$_3$
7.28 7.98 H$_5$, H$_6$
IR (Nujol)
Complex absorption OH/NH region
1665 cm$^{-1}$ CO
1628 cm$^{-1}$ CO
1610, 1542, 1520 cm$^{-1}$ aromatics

EXAMPLE 14

4'-[2-[bis-(isopropyl)-amino]-2-oxoethoxy]-2,6-dimethyl-(1,1'-biphenyl)-4-carboxylic acid Stage A (2,6-dimethyl-4-formylphenyl) trifluoromethane-sulfonate 4.3 ml of trifluoromethanesulfonic anhydride were added under an inert atmosphere at 0° C., to a mixture of 3.0 g of 3,6-dimethyl-4-hydroxy-benzaldehyde and 20 ml of pyridine and the mixture was stirred for 3 hours at ambient temperature. Then the reaction medium was poured into ice-cooled water and after extraction with dichloromethane, and drying of the organic phase over magnesium sulfate and concentrated to dryness under reduced pressure, the residue was chromatographed on silica, eluting with a cyclohexane/ethyl acetate mixture (9/1) to obtain 4.11 g of the expected product.

NMR (CDCl$_3$, 300 MHz)
2.49 (s) 6H Ph—C$\underline{H}_3$
7.66 (s) aromatic 2H's
9.97 (s)

Stage B 2,6-dimethyl-4'-[[(1,1-dimethylethyl)diphenyl-silyl]oxy]-(1,1'-biphenyl)-4-carboxaldehyde A mixture of 4 g of the product of Stage A, 1.58 g of lithium chloride, 600 mg of palladium tetrakis (triphenylphosphine), 15.56 g of stannylated derivative (Preparation 4) and 50 ml of dioxane was stirred for 16 hours at 100° C. under an inert gas atmosphere. After having evaporated the dioxane under reduced pressure, dichloromethane was added and the organic phase was washed with a saturated solution of potassium fluoride and dried over magnesium sulfate. The dichloromethane was evaporated and the residue was purified by chromatography on silica using a cyclohexane/ethyl acetate mixture (99/1) as eluant to obtain 0.392 g of the expected pure product.

IR (CHCl$_3$)
CO: 1693 cm$^{-1}$
aromatic: 1607, 1591, 1571, 1510 cm$^{-1}$
NMR (CDCl$_3$, 250 MHz)
1.14 (s) SitBu
2.03 (s) Ph—C$\underline{H}_3$
7.56 (s) aromatic H's in ortho position of the CO
6.83 (m) aromatic H's
7.30 to 7.80 aromatic H's
9.95 (s) CHO Stage C 2,6-dimethyl-4'-hydroxy-(1,1'-biphenyl)-4-carboxaldehyde 3.5 ml of tetrabutylammonium fluoride were added to a solution of 1.8 g of the protected biphenyl prepared in Stage B in 10 ml of tetrahydrofuran and the mixture was stirred for 10 minutes at ambient temperature. After evaporation under reduced pressure of the tetrahydrofuran, the residue was chromatographed on silica using a cyclohexane/ethyl acetate mixture (9/1) as eluant, 634 mg of the expected product were obtained.

IR (CHCl$_3$)
OH: 3597 cm$^{-1}$
CO: 1695 cm$^{-1}$
aromatic: 1613, 1603, 1592, 1518 cm$^{-1}$ Stage D N,N-bis-(isopropyl)-2-[[2',6'-dimethyl-4'-formyl-(1,1'-biphenyl)-4-yl]oxy]-acetamide The alkylation reaction was carried out with the procedure of Stage D of Example 13 and 189 mg of the product of Stage C were reacted to obtain 231 g of expected product.

IR (CHCl$_3$)
Absence of OH
CO: 1695, 1656 and 1637 cm$^{-1}$
aromatics: 1610, 1577, 1568, 1514 cm$^{-1}$ Stage E 4'-[2-[bis-(isopropyl)-amino]-2-oxoethoxy]-2,6-dimethyl-(1,1'-biphenyl)-4-carboxylic acid The oxidation reaction was carried out with the procedure of Stage C of Example 9, and 160 mg of the product of Stage D were reacted to obtain 118 mg of the expected product which was crystallized from ether.

NMR (CDCl$_3$, 250 MHz)
1.25 (d) 1.43 (d) CH(C$\underline{H}_3$)$_2$
3.45 (m) 4.14 (m) C$\underline{H}$(CH$_3$)$_2$
4.69 (s) OC$\underline{H}_2$CO
2.08 (s) Ph—C$\underline{H}_3$
7.04 (AA'BB') Ph—O
7.85 H$_3$, H$_5$ in ortho position of the CO
IR (CHCl$_3$)
acid 3520 cm$^{-1}$
CO: 1690, 1653 and 1636 cm$^{-1}$
aromatics: 1611, 1576, 1514 cm$^{-1}$

EXAMPLE 15

4'-[2-[bis-(isopropyl)-amino]-2-oxoethoxy]-2-(trifluoromethyl)-(1,1'-biphenyl)-4-carboxylic acid Stage A:

4'-(benzyloxy)-2-trifluoromethyl-(1,1'-biphenyl)-4-carboxaldehyde 0.911 g of 3-trifluoromethyl-4-bromo-benzaldehyde, 0.903 g of boronic acid of Preparation 2, 0.208 g of palladium tetrakis (triphenylphosphine), 1.24 g of tripotassium phosphate monohydrate and 10 ml of dioxane were mixed together under an inert gas atmosphere and the mixture was stirred at reflux for 3 hours. After dilution in water, extraction with ethyl acetate, ether and dichloromethane, the organic phases were dried over magnesium sulfate and evaporated under reduced pressure to obtain 1.584 g of the expected crude product. After purification by chromatography on silica, eluting with a cyclohexane/ethyl acetate mixture (95/5), 1.093 g of pure product were isolated with a Rf=0.33 (cyclohexane/ethyl acetate 8/2).

IR (CHCl$_3$)
2736, 1706 cm$^{-1}$ CHO 1611 (F), 1580, 1565 (sh), 1520 cm$^{-1}$ aromatics Stage B 4'-hydroxy-2-trifluoromethyl-(1,1'-biphenyl)-4-methanol 1) Debenzylation 308 mg of the product of Stage A and 290 mg of 9.5% palladium on activated charcoal were mixed with 15 ml of ethyl acetate overnight at 20° C. under a hydrogen atmosphere and then the reaction mixture was filtered. After evaporation under reduced pressure, 215.7 mg of a crude product were obtained which was used directly as is in the following reduction reaction.

2) Reduction 215.7 mg of the previous product and 48 mg of 95% boron and sodium hydride were mixed at 20° C. for 3 hours under an argon atmosphere with 3 ml of methanol and then the reaction medium was evaporated under reduced pressure. The residue was taken up in dichloromethane and the organic phase was washed with a saturated solution of ammonium chloride, dried over magnesium sulfate and evaporated under reduced pressure to obtain 113 mg of a white powder which was purified by chromatography on a silica column, eluting with a cyclohexane/ethyl acetate mixture (8/2) to obtain 99 mg of the expected product with a Rf=0.20 (cyclohexane/ethyl acetate 7/3) and a melting point of 132°–134 ° C.

IR (Nujol)
Absence of C=O
General absorption OH/NH region
Aromatic: 1615, 1600, 1520 (sh), 1492 cm$^{-1}$
Stage C 4'-hydroxy-2-trifluoromethyl-(1,1'-biphenyl)-4-carboxylic acid Oxidation was carried out with 99 mg of the product of Stage B with Jones' reagent under the conditions as described in Example 2 Stage C to obtain 98.5 mg of the expected product with a Rf=0.33 (dichloromethane/methanol 9/1).

Stage D

4'-[2-[isopropyl]-amino]-2-oxoethoxy]-2-(trifluoromethyl)-(1,1'-biphenyl)-4-carboxylic acid A mixture of 505 mg of the product of Stage C, 1.8 ml of 2N sodium hydroxide, 8 ml of dimethyl-sulfoxide was stirred at 80° C. for 30 minutes and 397 mg of N,N-bis-(isopropyl)-2-bromo acetamide were added. After stirring for 2 hours at 80° C., the reaction mixture was poured into 80 ml of water and extraction was carried out with ethyl acetate, followed by washing with water until the dimethylsulfoxide was eliminated. The mixture was washed with 2N sodium hydroxide, dried and evaporated under reduced pressure to obtain 424 mg of crude product which was purified by chromatography on silica, eluting with a dichloromethane/methanol mixture (95/5) to obtain 124 mg of the expected pure product with a Rf=0.26 (dichloromethane/methanol 9/1).

NMR (CDCl$_3$, 250 MHz)
1.24 (d) 1.43 (d) CH(C$\underline{H}_3$)$_2$)
3.46 (m) 4.11 (m) C$\underline{H}$(CH$_3$)$_2$)
4.69 (s) OC$\underline{H}_2$CO
7.01 and 7.26 (AA'BB') aromatic H Ar—O
7.46 (d) H$_6$ of ArCOOH
8.25 (dd) H$_5$ of ArCOOH
8.47 (d) H$_3$ of ArCOOH
IR (Nujol)
acid OH 3520 cm$^{-1}$+ general absorption
acid C=O 1738 (sh) 1702 cm$^{-1}$ (max)
amide C=O 1657 (sh) 1638 cm$^{-1}$ (max)
aromatic: 1618 (F), 1582, 1570, 1520, 1490 cm$^{-1}$

EXAMPLE 16

4'-[2-[bis-(isopropyl)-amino]-2-oxoethoxy]-2,6-dichloro-(1,1'-biphenyl)-4-carboxylic acid Stage A 3,5-dichloro-4-hydroxy-benzaldehyde 15 g of hydroxy-4-benzaldehyde in 75 ml of thionyl chloride was stirred at reflux for 36 hours and then the reaction medium was evaporated under reduced pressure to obtain the expected crude product which was crystallized from an acetone/n-pentane mixture to obtain 20 g of an 85/15 mixture of dichlorinated/monochlorinated product. Crystallization from a cyclohexane/acetone mixture (4/1) allowed the pure dichlorinated product to be obtained with a Rf=0.15 (dichloromethane/methanol 99/1).

IR (CHCl$_3$)
—OH 3511 cm$^{-1}$
C=O 1600 cm$^{-1}$
aromatics 1600, 1588, 1574 cm$^{-1}$
Stage B (2,6-dichloro-3-formylphenyl) trifluoromethane-sulfonate 15 ml of trifluoromethanesulfonic anhydride were added dropwise at 0°–5° C. under an inert gas atmosphere to a solution of 14.6 g of the mixture of products obtained in Stage A in 100 ml of pyridine the mixture was stirred for 90 minutes. The reaction medium was poured into ice-cooled water and then extraction was carried out with ethyl acetate. The organic phase was dried over magnesium sulfate, filtered and evaporated under reduced pressure to obtain 25 g of crude product which was chromatographed on silica, eluting with a cyclohexane/ethyl acetate mixture (9/1) to obtain 20.22 g of the mixture of the expected product dichlorinated 92%/monochlorinated 8% (dichlorinated: Rf=0.53 cyclohexane/ethyl acetate 7/3).

IR (CHCl$_3$) (dichlorinated)
Absence of OH
C=O 1711 cm$^{-1}$
OSO$_2$CF$_3$ 1434, 1133 cm$^{-1}$
aromatics 1573 cm$^{-1}$
Stage C 2,6-dichloro-4'-[[(1,1-dimethylethyl)diphenyl-silyl]oxy]-(1,1'-biphenyl)-4-carboxaldehyde 8.2 g of potassium bromide, 15.8 g of monohydrated potassium phosphate, 22.4 g of boronic acid (Preparation 3) and 3.6 g of palladium tetrakis triphenylphosphine were added to a solution under an inert gas atmosphere of 20.2 g of the product of Stage B, in 125 ml of dioxane and the mixture was refluxed for 15 hours. Next, the reaction medium was filtered and the residue was chromatographed on silica, eluting with a cyclohexane/ethyl acetate mixture 92/8, 9/1 and finally 8/2 to obtain 12.5 g of product containing 38% of monochlorinated product and 62% of dichlorinated product with a Rf =0.63 (cyclohexane/ethyl acetate 7/3).

IR (CHCl$_3$)
C=O 1708 cm$^{-1}$
aromatics 1609, 1592, 1548, 1516 cm$^{-1}$
Stage D 2,6-dichloro-4'-hydroxy-(1,1'-biphenyl)-4-carboxaldehyde 2 ml of a 1M solution of tetrabutylammonium fluoride were added under an inert gas atmosphere to a solution of 1.5 g of the dichlorinated product of Stage C in 5 ml of tetrahydrofuran and the mixture was stirred at ambient temperature for 30 minutes to obtain the desired product.

IR (CHCl$_3$)
CHO 1707 cm$^{-1}$
Ar 1612, 1593, 1549, 1519 cm$^{-1}$
NMR (CDCl$_3$)
4.97 (s) OH
6.97 and 7.16 (AA'BB') aromatic H's (Ph—OH)
7.89 (s) H$_4$, H$_6$ (PhCHO)
9.96 (s) C$\underline{H}$O
Stage E N,N-bis-(isopropyl)-2-[[2',6'-dichloro-4'-formyl-(1,1'-biphenyl)-4-yl]oxy]-acetamide An alkylation was carried out starting with 116.4 mg of the dichlorinated product of Stage D with bromoacetamide (Preparation 9) under the conditions described in Example 2, Stage A to obtain 124 mg of the expected product with a Rf=0.26 (cyclohexane/ethyl acetate 8/2).

IR (Nujol)
acid, amide C=O 1709 cm$^{-1}$, 1640 cm$^{-1}$
aromatic: 1610, 1580, 1550, 1518 cm$^{-1}$ Stage F 4'-[2-[bis-(isopropyl)-amino]-2-oxoethoxy]-2,6-dichloro-(1,1'-biphenyl)-4-carboxylic acid 124 mg of the product of Stage E were mixed with 2 ml of tetrahydrofuran, 3.5 ml of water, 98 mg of sodium chlorite monohydrate and 87 mg of amidosulfonic acid and the mixture was stirred for 90 minutes at ambient temperature and evaporated under reduced pressure to obtain a residue which was obtained which is taken up in ethyl acetate. The organic phase was washed with 1N sodium hydroxide, dried over magnesium sulfate and evaporated under reduced pressure to obtain 97.8 mg of the expected product with a Rf=0.26 (cyclohexane/ethyl acetate 8/2).

NMR (CD$_3$OD, 300 MHz)
1.27 (d, J=6.5) 1.42 (d, J=6.5) CH(C$\underline{H}_3$)$_2$
3.57 (septet, J=6.5) 4.13 (septet, J=6.5) C$\underline{H}$(CH$_3$)$_2$
4.77 (s) OC$\underline{H}_2$CO
7.07 and 7.18 AA'BB' aromatic H (Ar—O)
8.02 (s) H$_3$, H$_5$ (Ar—COOH)

IR (CHCl$_3$)
acid C=O 1704 cm$^{-1}$
amide C=O 1636 cm$^{-1}$
aromatic: 1610, 1581, 1543, 1517 cm$^{-1}$

EXAMPLE 17

4'-[2-[bis-(isopropyl)-amino]-2-oxoethoxy]-2,6-difluoro-(1,1'-biphenyl)-4-carboxylic acid Stage A Protection 2-[(3,5-difluorobenzyloxy]-tetrahydropyran.

1.28 g of 3,5-difluorobenzyl alcohol, 1.3 ml of 3,4-dihydropyran and 155 mg of p-toluene sulfonic acid in 20 ml of dioxane were stirred under an argon atmosphere at ambient temperature for 2 hours 30 minutes and then the reaction mixture was poured into a saturated solution of sodium bicarbonate. The dioxane was evaporated under reduced pressure and the aqueous phase was extracted with ethyl acetate. The organic phase was dried over magnesium sulfate and evaporated under reduced pressure to obtain 1.81 g of the expected with a Rf=0.42 (cyclohexane/ethyl acetate 9/1).

IR (CHCl$_3$)
Absence of OH
1632, 1602 cm$^{-1}$ aromatics

Stage B 2,6-difluoro-4'-benzyloxy-(1,1'-biphenyl)-4-methanol 3.7 ml of a solution (1.5M) of n-butyllithium in hexane were added dropwise under an inert atmosphere at −78° C. to a solution of 1.045 g of the product of Stage A in 20 ml of tetrahydrofuran, and after stirring for 15 minutes at −78° C., 5.5 ml of a solution (1.0M) of zinc chloride in tetrahydrofuran were added. At the end of 30 minutes at −78° C., the temperature was allowed to rise to 20° C. and 1.44 g of 1-bromo 4-(benzyloxy) benzene (Preparation 2, Stage A) and 265 mg of palladium tetrakis (triphenyl-phosphine) palladium are added. The reaction medium is refluxed for 5 hours and then was poured into a saturated solution of ammonium chloride. Extraction was carried out with dichloromethane and the organic phase was dried over magnesium sulfate and evaporated under reduced pressure to obtain a yellow oil which was used as is in the hydrolysis reaction.

2.3 ml of 2N hydrochloric acid were added to the crude oil dissolved in 30 ml of methanol and the mixture was stirred at 20° C. for 24 hours. The reaction medium was poured into a saturated solution of sodium bicarbonate and the methanol was evaporated under reduced pressure. The aqueous phase was extracted with methylene chloride and the organic phase was dried over magnesium sulfate, filtered and evaporated under reduced pressure to obtain 1.85 g of product which was purified by chromatography on silica, eluting with a cyclohexane/ethyl acetate mixture (9/1) to obtain 873 mg of desired product with a Rf=0.32 (cyclohexane/ethyl acetate 7/3).

IR (Nujol)
General absorption OH/NH
1640, 1612, 1582, 1569, 1528, 1492 cm$^{-1}$ aromatics Stage C 2,6-difluoro-4'-(benzyloxy)-(1,1'-biphenyl)-4-carboxylic acid An oxidation was carried out with 107 mg of the product of Stage B, with Jones' reagent under the conditions as described in Example 2, Stage C to obtain 86 mg of the expected product with a Rf=0.06 cyclohexane/ethyl acetate 7/3).

IR (Nujol)
General absorption OH/NH
1704 cm$^{-1}$ C=O
1610, 1580, 1564, 1522 cm$^{-1}$ aromatics Stage D 2,6-difluoro-4'-hydroxy-(1,1'-biphenyl)-4-carboxylic acid 342 mg of the product of Stage C were stirred overnight at 20° C. under a hydrogen atmosphere in 30 ml of ethyl acetate and with 113 mg of 9.5% palladium on activated charcoal. The reaction mixture was filtered and evaporated under reduced pressure to obtain 232.6 mg of the expected product.

IR (Nujol)
General absorption OH/NH
1705 cm$^{-1}$ C=O
1615, 1597, 1572, 1529 cm$^{-1}$ aromatics Stage E 4'-[2-[bis(isopropyl)-amino]-2-oxoethoxy]-2,6-difluoro-(1,1'-biphenyl)-4-carboxylic acid An alkylation was carried out with 370 mg of the product of Stage D with 428 mg of bromoacetamide (Preparation 9) under the conditions as described in Example 13, Stage D to obtain 282 mg of the expected product with a Rf=0.35 dichloromethane/methanol/acetic acid 95/4/1).

NMR (CD$_3$OD, 300 MHz)
1.25 (d) 1.44 (d) CH(C$\underline{H}_3$)$_2$
3.47 (m) 4.09 (m) C$\underline{H}$(CH$_3$)$_2$
4.70 (s) OC$\underline{H}_2$CO
7.06 (d) and 7.45 (d) aromatic H (Ph—O)
7.70 (d, J=8) H$_3$, H$_5$ (Ph—COOH)
5.20 (broadened) mobile H COOH IR (CHCl$_3$)

acid C=O 1700 cm$^{-1}$
amide C=O 1637 cm$^{-1}$

EXAMPLE 18

4'-[2-[bis-(isopropyl)-amino]-2-oxoethoxy]-2',6'-dichloro-(1,1'-biphenyl)-4-carboxylic acid Stage A 3,5-dichloro-1-[[(1,1-dimethylethyl) dimethylsilyl]-oxy]-benzene A mixture of 5.02 g of 3,5-dichlorophenol, 5.57 g of tert-butyldimethylsilyl chloride, 5.24 g of imidazole and 50 ml of N,N-dimethylformamide was stirred at 20 °C. for 3 hours and then was poured into a saturated solution of ammonium chloride and extracted with dichloromethane. The organic phase was dried over magnesium sulfate and concentrated under reduced pressure to obtain 9 g of residue is obtained which was chromatographed on silica, eluant: essence G with 1/00 of triethylamine to obtain 7.45 g of the expected product.

NMR (CDCl$_3$, 200 MHz)
7.05 (s) 1H H4
6.8 (s) 2H H$_2$, H$_6$
1.05 (s) 9H Si—C(CH$_3$)$_3$
0.3 (s) 6H Si—(CH$_3$)$_2$

Stage B methyl 2',6'-dichloro-4'-hydroxy-(1,1'-biphenyl)-4-carboxylate

1) Coupling 3.9 ml of n-butyllithium (1.16M) in hexane and then 4.5 ml of zinc chloride in solution (1M) in tetrahydrofuran were introduced at −78° C. under an inert gas atmosphere into a solution of 1.04 g of the chlorinated derivative of Stage A in 10 ml of tetrahydrofuran, and after stirring for 30 minutes at this temperature and after having allowed the temperature to progressively rise to 20° C., 0.966 g of methyl 4-bromo-benzoate and 0.217 g of palladium tetrakis (triphenylphosphine) were added. The mixture was refluxed for 24 hours and was then poured into a saturated solution of ammonium chloride. Extraction was carried out with dichloromethane and the organic phases were dried and concentrated to dryness under reduced pressure to obtain 1.93 g of an oil which was used as is in the following stage.

2) Deprotection 5 ml of tetrabutylammonium fluoride were added at 0° C. under an inert gas atmosphere to 1.709 g of the crude product from the preceding stage in 10 ml of tetrahydrofuran and the mixture was stirred for 90 minutes. The reaction mixture was then poured into a saturated solution of ammonium chloride and extraction was carried out with dichloromethane. The organic phases were dried with magnesium sulfate and concentrated to dryness under reduced pressure to obtain 2.56 g of an oil which was chromatographed on silica with a cyclohexane/ethyl acetate mixture (90/10) to obtain 260 mg of a mixture of the expected product and the corresponding butyl ester.

Stage C

4'-[2-[bis-(isopropyl)-amino]-2-oxoethoxy]-2',6'-dichloro-(1,1'-biphenyl)-4-carboxylic acid After refluxing for 90 minutes a mixture of by 194.3 mg of the ester mixture obtained in Stage B, 0.65 ml of 2N sodium hydroxide and 4 ml of dimethylsulfoxide, 144 mg of N,N-bis-(isopropyl)-2-bromo-acetamide (Preparation 8) was added. The mixture was stirred at reflux overnight and was then poured into water. Extraction was carried out with ethyl acetate and the organic phases were dried with magnesium sulfate. The mixture was concentrated under reduced pressure until 196 mg of an oil were obtained which was purified by chromatography on a silica column with a dichloromethane/methanol eluant mixture (90/10) to obtain 51 mg of the expected product with a Rf=0.5 (dichloromethane/methanol 9/1.

IR (Nujol)
Absorption OH/NH
C=O 1712 cm$^{-1}$
C=O amide 1628, 1614, 1600 (sh), 1552, 1516 cm$^{-1}$+ aromatics
NMR (DMSO, 250 MHz)
13.07 (broad) CO$_2$H
7.38 (d) 8.02 (d) aromatic H (Ar—COOH)
7.17 (s) 2H H'$_3$ and H'$_5$
4.88 (s) 2H OCH$_2$CO
3.49 (m) 3.91 (m) CH(CH$_3$)$_2$
1.19 (d) 1.31 (d) CH(CH$_3$)$_2$

EXAMPLE 19

4'-[[bis-(isopropyl)-amino]-carbonyl]-2'-iodo, 6'-nitro-(1,1'-biphenyl)-4-carboxylic acid Stage A N,N-bis-(isopropyl)-4-chloro-3,5-dinitro-benzenecarboxamide 3 ml of SOCl$_2$ and about 5 ml of dimethylformamide were added dropwise under an inert gas atmosphere to a solution of 10 g of 4-chloro-3,5-dinitro-benzene-1-carboxylic acid in 300 ml of dichloromethane and the mixture was refluxed for 20 hours. Next, 300 ml of dichloromethane were added and the reaction mixture was cooled to 0° C. 18 ml of diisopropylamine were added and the mixture was stirred at ambient temperature for 12 hours. The reaction mixture was diluted with 250 ml of 2N hydrochloric acid and extraction was carried out with dichloromethane, followed by evaporation under reduced pressure. Ether was added and the precipitate (iPr$_2$NH$_2^+$Cl$^-$) was filtered. The ethereal phase was washed with sodium bicarbonate, and then concentrated under reduced pressure to obtain 5.31 g of dry extract corresponding to the expected product with a Rf=0.5 (cyclohexane/ethyl acetate 70/30).

IR (CHCl$_3$)
C=O, aromatics, NO$_2$ 1637 cm$^{-1}$, 1610 cm$^{-1}$,1550 cm$^{-1}$
NMR (200 MHz CDCl$_3$)
1.2 to 1.5 CH(CH$_3$)$_2$
3.5 to 3.7 CH(CH$_3$)$_2$
7.9 aromatic H's Stage B methyl 2'-amino-4'-[[bis-(isopropyl)-amino]-carbonyl]-6'-nitro-(1,1'-biphenyl)-4-carboxylate (Product A) and methyl 4'-[[bis-(isopropyl)-amino]-carbonyl]-2',6'-dinitro-(1,1'-biphenyl)-4-carboxylate (Product B)

1.67 g of the amide of Stage A, 1.39 g of methyl iodo benzoate (Preparation 7), 2.5 g of copper and 4 ml of dimethylformamide were mixed together in an autoclave at 200° C. for 90 minutes. After evaporation of the dimethylformamide, extraction was carried out with methylene chloride, followed by concentration under reduced pressure and purification by chromatography on silica, eluting with a cyclohexane/ethyl acetate mixture (7/3) to obtain 337.5 mg of Product A and 766 mg of Product B.

Product A
IR (CHCl$_3$)
1723 cm$^{-1}$ CO
1625 cm$^{-1}$ amide
1610, 1535 cm$^{-1}$ aromatic+NO$_2$
3494, 3404 cm$^{-1}$ —NH$_2$
Product B
IR (CHCl$_3$)
1724 cm$^{-1}$ CO
1636 cm$^{-1}$ amide
1612, 1546 cm$^{-1}$ aromatic+NO$_2$
Stage C 2'-amino-4'-[[bis-(isopropyl)-amino]-carbonyl]-6'-nitro-(1,1'-biphenyl)-4-carboxylic acid 0.64 ml of 2N sodium hydroxide were added to a solution of 235 mg of product A in 4 ml of tetrahydrofuran and the mixture was heated under refluxed for 2 hours. Then, the reaction mixture was diluted with 10 ml of water and the pH was adjusted to 9 with 1N hydrochloric acid. Washing was carried out with ethyl acetate and the pH is adjusted to 5 with 1N hydrochloric acid. Extraction was carried out with ether and the ethereal phases were dried with MgSO4, followed by evaporation under reduced pressure. The residue was crystallized from ether to obtain 191.7 mg of the expected product.
IR (CHCl$_3$)
1735, 1696, 1624 cm$^{-1}$ CO
1536, 1487 cm$^{-1}$ aromatic+NO$_2$
3500, 3410 cm$^{-1}$ —NH$_2$
Stage D 4'-[[bis-(isopropyl)-amino]-carbonyl]-2'-iodo-6'-nitro-(1,1'-biphenyl)-4-carboxylic acid 2.7 mg of NaNO$_2$ in solution in water were added dropwise to a solution of 76.6 mg of the product of Stage C and 0.6 ml of concentrated sulfuric acid cooled to 0° C. and the temperature was maintained at 0° C. for 3 hours. The reaction medium was poured into 20 g of ice and finally 100 mg of potassium iodide in 1.5 ml water were added dropwise. After having heated the mixture to 80° C. for 15 minutes and cooled it to ambient temperature, extraction was carried out with 10 ml of dichloromethane. The organic phase was dried, concentrated under reduced pressure and purified by chromatography on silica with a cyclohexane/ethyl acetate eluant mixture 50/50 with the addition of 1% of acetic acid to obtain 82.2 mg of the expected product with a Rf=0.34 (dichloromethane/methanol).
NMR (CDCl$_3$, 250 MHz)
1.2 to 1.4 CH(C$\underline{H}$$_3$)$_2$
3.7 C$\underline{H}$(CH$_3$)$_2$
7.32; 8.2 aromatic H (Ar—COOH)
7.84 (d) 8.14 (d) coupled 2H's in meta position (Ar—CONiPr$_2$)

EXAMPLE 20

4'-[[bis-(isopropyl)-amino]-carbonyl]-2',6'-dinitro-(1,1'-biphenyl)-4-carboxylic acid Using the procedure of Example 19, Stage C, 244.4 mg of product B prepared in Example 19, Stage B were reacted to obtain 244.5 mg of the expected product with a Rf=0.146 (cyclohexane/ethyl acetate 1/1).
IR (CHCl$_3$)
CO (acid) 1696 cm$^{-1}$ aromatic, amide, NO$_2$ 1628 (F), 1609, 1567 (sh), 1555 (sh) 1541 (F), 1530 cm$^{-1}$ (sh)
NMR (CDCl$_3$, 250 MHz)
1.2 to 1.7 CH(C$\underline{H}$$_3$)$_2$
3.75 C$\underline{H}$(CH$_3$)$_2$
7.39; 8.20 Ar—COOH
8.03 (s) aromatic H's (ArCONiPr$_2$)

EXAMPLE 21

4'-[[bis-(isopropyl)-amino]-carbonyl]-2',6'-diamino-(1,1'-biphenyl)-4-carboxylic acid A mixture of 349.7 mg of the product of Example 20, 1.55 g of stannous chloride and 10 ml of ethanol was refluxed for one hour, under an inert gas atmosphere, and then 30 ml of water, then ammonia were added successively to adjust the pH to 7. Extraction was carried out with ethyl acetate and the aqueous phase was adjusted to a pH of 5 which led to the formation of a precipitate which was extracted with ether. The organic phases were dried over magnesium sulfate, followed by filtration and concentration to obtain 349.6 mg of the expected product with a Rf=0.13 (dichloromethane/methanol 9/1).
IR (CHCl$_3$)
CO 1696, 1613 cm$^{-1}$
=C—NH$_2$ 3490, 3400 cm$^{-1}$
aromatic+NH$_2$ 1569, 1464 cm$^{-1}$
NMR (CDCl$_3$, 250 MHz)
1.2 to 1.51 (s,b) CH(C$\underline{H}$$_3$)$_2$
3.5 to 4.05 (b) C$\underline{H}$(CH$_3$)$_2$
7.44 (d); 8.19 (d) aromatic H's (Ar—COOH)
6.13 (s) aromatic H's alpha NH$_2$

EXAMPLE 22 sodium 2'-amino-4'-[[bis-(isopropyl)-amino]-carbonyl]-6'-nitro-(1,1'-biphenyl)-4-carboxylate 0.64 ml of a solution of 2N NaOH were added under an inert atmosphere to a solution of 235.3 mg of the biphenyl of Stage B (Product A) of Example 19 in 4 ml of tetrahydrofuran and the mixture was stirred for 4 hours at ambient temperature, then for 90 minutes at reflux. After cooling the reaction medium, the pH was adjusted to 3 by the addition of 1N hydrochloric acid and extraction was carried out with ether. The ethereal solution was washed with 3.7 ml of 0.1N sodium hydroxide and after separation and lyophilization of the aqueous phase, 74.5 mg of the expected product were obtained.
NMR (D$_2$O, 250 MHz)
1.21 (d) to 1.5 (d) CH(C$\underline{H}$3)$_2$
3.77 (m) and 3.9 (m) C$\underline{H}$(CH3)$_2$
7.11 (d) H'$_3$
7.37 (d) H'$_5$
7.39 and 7.99 (AA'BB') aromatic H's (Ar—COONa)

EXAMPLE 23

4'-[[bis-(isopropyl)-amino]-carbonyl]-2',6'-diiodo-(1,1'-biphenyl)-4-carboxylic acid Using the procedure of Example 19D, 226 g of the product of Example 21 were reacted to obtain an 87.7 mg of the expected product with a Rf=0.47 (methylene chloride/methanol 90/10).
IR (Nujol)
1690, 1628 cm$^{-1}$ CO
1612, 1565, 1510 cm$^{-1}$ aromatic NMR (CDCl$_3$, 300 MHz)
1.2 to 1.7 CH(C$\underline{H}_3$)$_2$
3.4 to 4.0 C$\underline{H}$(CH$_3$)$_2$
7.25, 8.24 Ar—CO
7.88 (s) alpha aromatic H's of I

EXAMPLE 24

4'-[[bis-(isopropyl)-amino]-carbonyl]-2',6'-dibromo-(1,1'-biphenyl)-4-carboxylic acid A solution of 100 mg of the product of Example 21 in 2 ml of water and 0.34 ml of hydrobromic acid was prepared at 0° C. and 29 mg of sodium nitrite in solution in 0.5 ml of water were added. Then this solution was added at 0° C. dropwise to a mixture stirred at 0° C. of 121 mg of copper bromide in 0.4 ml of 66% hydrobromic acid and the mixture was stirred at ambient temperature for 16 hours. After dilution in 20 ml of ice-cooled water and acidification by 1N hydrochloric acid to obtain a pH of 1, extraction with ether was performed. The organic phases were dried and concentrated under reduced pressure. The residue was chromatographed on silica with a cyclohexane/ethyl acetate eluant mixture 50/50 with 1% of acetic acid to obtain and 43.9 mg of the expected product with a Rf=0.47 (methylene chloride/methanol 90/10).

NMR (CDCl$_3$, 250 MHz)
1.2 to 1.6 CH(C$\underline{H}_3$)$_2$
3.4 to 3.95 C$\underline{H}$(CH$_3$)$_2$
7.35; 8.23 Ar—CO
7.59 (s) alpha aromatic H's Br

EXAMPLE 25

4'-[2-[bis-(isopropyl)-amino]-2-oxoethoxy]-N-(hydroxy)-(1,1'-biphenyl)-4-carboxamide Stage A 4'-[2-[bis-(isopropyl)-amino]-2-oxoethoxy]-N-(benzyloxy)-(1,1'-biphenyl)-4-carboxamide 170 mg of the product of Example 2 were mixed under an inert gas atmosphere with 80 mg of benzylhydroxylamine hydrochloride, 0.071 ml of triethylamine, 70 mg of hydroxybenzotriazole, 120 mg of dicyclohexyl carbodiimide and 10 ml of chloroform and the mixture was stirred for 8 hours at ambient temperature. The organic phase was dried over magnesium sulfate, filtered and evaporated to dryness under reduced pressure. The crude product was chromatographed on silica (eluting with a cyclohexane/ethyl acetate mixture 70/30) to obtain 100 mg of the expected product.

NMR (CDCl$_3$, 300 MHz)
5.06 (s) C$\underline{H}_2$Ph

Stage B

4'-[2-[bis-(isopropyl)-amino]-2-oxoethoxy]-N-(hydroxy)-(1,1'-biphenyl)-4-carboxamide 80 mg of the benzyl hydroxamate of Stage A were mixed with 50 mg of palladium on charcoal, 5 ml of ethanol and 40 ml of ethyl acetate, and the mixture was stirred for 8 hours under a hydrogen atmosphere. The reaction medium was filtered and evaporated under reduced pressure. The residue was purified by chromatography on silica, eluting with a mixture of cyclohexane/ethyl acetate (50/50) then ethyl acetate and finally ethyl acetate/acetic acid 99/1. The product was finally crystallized from ethyl acetate to obtain 5.2 mg of the expected product.

IR (CHCl$_3$)
carbonyl 1630 cm$^{-1}$
aromatic 1606, 1584, 1555, 1494 cm$^{-1}$
NMR (CDCl$_3$, 250 MHz)
1.24 (d) 1.43 (d) CH(C$\underline{H}_3$)$_2$
3.46 (m) 4.08 (m) C$\underline{H}$(CH$_3$)$_2$
4.67 O—CH$_2$—CO
7.00 (d) 7.49 (d) Ph—O
7.53 (d) 7.57 (d) Ph—CO

EXAMPLE 26

N,N-bis-(isopropyl)-2[[4'-nitro-(1,1'-biphenyl)-4-yl]oxy]-acetamide

The product was prepared as in Example 2, Stage A starting with 900 mg of 4'-hydroxy-(4-nitro biphenyl) (Aldrich) and 958 mg of N,N-bis-(isopropyl)-2-bromo-acetamide (Preparation 8) to obtain 1.26 g of the expected product.

IR (CHCl$_3$)
Absence of OH
CO 1655, 1638 cm$^{-1}$
aromatic+NO$_2$ 1600, 1580, 1520, 1490 cm$^{-1}$
NMR (CDCl$_3$)
1.24 (d) 1.42 (d) CH(C$\underline{H}_3$)$_2$
3.46 (m) 4.18 (m) C$\underline{H}$(CH$_3$)$_2$
4.69 (s) O—C$\underline{H}_2$—CO
7.07 (d) 7.57 (d) aromatic H's (Ar—O)
7.69 (d) 8.27 aromatic H's (Ar—NO$_2$)
Microanalysis
calculated % C 67.40 % H 6.79 % N 7.86
found C 67.3 H 6.8N 7.8

EXAMPLE 27

N,N-bis(isopropyl)-2[[4'-cyano-(1,1'-biphenyl)-4-yl]oxy]-acetamide

The product was prepared as in Example 2, Stage A starting with 780 mg of 4'-hydroxy-(4-biphenyl carbonitrile) (Aldrich) and 1.33 g of N,N-bis(1-methylethyl)-2-bromo-acetamide (Preparation 8) to obtain 1.2 g of the expected product.

IR (CHCl$_3$)
CN 2229 cm$^{-1}$
CO 1656 and 1638 cm$^{-1}$
aromatics 1606, 1584, 1518 and 1495 cm$^{-1}$
NMR (CDCl$_3$, 250 MHz)
1.24 (d) 1.42 (d) CH(C$\underline{H}_3$)$_2$
3.45 (m) 4,.8 (m) C$\underline{H}$(CH$_3$)$_2$
4.68 (s) O—CH$_2$—CO
7.06 7.53 aromatics
7.67 (AA'BB') aromatics

EXAMPLE 28

N,N-bis-(isopropyl)-2[[4'-1H-tetrazol-5-yl)-(1,1'-biphenyl)-4-yl]oxy]-acetamide

A mixture of 800 mg of the product of Example 27 and 1.4 ml of azido terbutyl tin (Bu$_3$SnN$_3$) in 4 ml of anhydrous toluene was refluxed for 12 hours. After having bubbled gaseous hydrochloric acid through the mixture for a few seconds, the precipitate was filtered to obtain 931 mg of the expected product.

IR (Nujol)
Complex absorption OH/NH
CO 1626 cm$^{-1}$
aromatics, tetrazole 1603, 1585, 1567, 1558 and 1518 cm$^{-1}$ NMR (DMSO, 250 MHz)
1.19 (d) 1.32 (d) CH(C$\underline{H}_3$)$_2$
3.49 (m) 4.00 (m) C$\underline{H}$(CH$_3$)$_2$
4.78 (s) O—CH$_2$—CO
7.04 and 7.72 aromatics
7.88 and 8.10 aromatics Pharmacological study The test for measuring the 5-α-reductase activity took place in vitro by incubating the enzyme and its substrate (testosterone) and measuring by HPLC chromatography the quantity of 5-α reduced metabolites formed (dihydrotestosterone (DHT) and 5-α-androstane-diol). Homogenates of human prostates were used, obtained by radical prostatectomies due to benign hyperplasia of the prostate (BHP): PH6.

Method
Preparation of the homogenate

The prostate was collected as soon as it left the operating theater suite and was packed in aluminum foil placed in a container filled with dry ice. In the laboratory, if the homogenate was not prepared immediately, the prostate could be kept at −80° C. The prostate was shredded over ice into very small pieces, which were homogenized in a medium A (20 mM of potassium phosphate, pH 6.5; 0.32M of sucrose; 1 mM of dithiotreitol (DTT); 50 uM NADPH), in a polytron, then in a Potter glass flask. After centrifuging at 140,000 g for 60 minutes at 4° C., the pellets obtained were suspended in 10 to 20 ml of medium B (20 nM of potassium phosphate, pH 6.5; 20% of glycerol; 1 mM of dithiothreitol). The medium was distributed in Nunc tubes kept at −80° C. Determination of the proteins was carried out on a small amount of homogenate for its future use in the test and it was therefore assured of having at least 10 mg of proteins/ml of homogenate.

Measurement of the 5-α-reductase activity

Incubation was carried out at a pH of 5.5 at the rate of 1 ml of medium/tube in the presence of citrate (normal medium and pH of the prostate).

1) Preparation of the substrate (S) which was the mixture of "unlabelled" testosterone and "tritiated" testosterone with an isotopic dilution of 100 in a trisodium citrate buffer pH 5.0 a) 40 mM of trisodium citrate buffer: 11.76 g of 3 Na-citrate, 2H$_2$O (Merk ref. Art 6448) were weighed and dissolved in 1 liter of distilled water (Milli-Q) and the solution was adjusted to pH of 5.0.

b) mixture of "unlabelled" testosterone and "tritiated" testosterone with an isotopic dilution of 100: To obtain a solution of testosterone of 1 mM, 2.88 mg of "unlabelled" testosterone were weighed and dissolved in 10 ml of ethanol. This solution was diluted to 0.99/1000, that is 9.9 μl in 10 ml of citrate buffer (=10$^{-6}$M solution). 9 μl of $^3$H-testosterone (NET-370) were added to 10 ml of the preceding solution (=isotopic dilution of 100). The substrate (S) was ready.

2) Preparation of enzyme+DTT+NADPH mixture a) Potassium phosphate buffer, 40 mM, pH 6.5:
5.44 g de KH$_2$PO$_4$ (Riedel de Haen ref. 30407) was weighed and dissolved in 1 liter of distilled water (Milli-Q) and the solution was adjusted to a pH of 6.5.

b) 1 mM DTT (Sigma)
3.1 mg of DTT were weighed and dissolved in 1 ml of phosphate buffer.

c) 500 μM NADPH (Sigma)
8.33 mg of NADPH were weighed and dissolved in 1 ml of phosphate buffer.

d) enzyme+DTT+NADPH mixture (E):
For one test, 0.5 mg of proteins of prostate homogenate, 50 μl of DTT and 50 μl of NADPH were mixed together at 4° C. and the mixture was made up to 500 μl with the phosphate buffer.

3) Incubation (5α-reduction)

One tube was prepared for each test and 500 μl of (S) and 10 μl of inhibitor at the desired concentration (or ethanol for the controls) are put in each tube. The tubes containing mixture (S) and the flask containing mixture (E) were pre-incubated in a water bath for 3 to 5 minutes.

To start the reaction, 500 μl of E were transferred rapidly into each tube containing S+the inhibitor and the mixture was incubated at 37° C. with gentle stirring for 30 minutes. The reaction was stopped at the end of the incubation by putting the tubes into ice.

4) Extraction

As soon as the reaction had stopped, 2 ml of ethyl acetate were added to each tube and the mixture was stirred in a multi-tube vortex shaker for 1 minute. The solution was left to decant for 10 minutes and then 1.6 ml of the (upper) organic phase of the extract (=80%) were recovered into other tubes. After total evaporation of the ethyl acetate, 800 μl of the HPLC chromatography mobile phase were added to each tube.

5) HPLC chromatography

The amounts of metabolites produced during the incubation were measured by separating the compounds formed by reversed-phase high performance liquid chromatography (HPLC). An ODS-Hypersil column (diameter of the particles=5 μm) and a mobile phase composed of MeOH/THF/H$_2$O in a ratio of 45/15/40 were used. The extract collected after extraction was injected automatically into the HPLC system and due to the in-line system for measuring radioactivity (Berthold), only the radioactive metabolites, thus formed from the testosterone labelled with the substrate, were evaluated. This measurement was very sensitive and eliminated all the possible endogenous products.

Expression of the results and methods of calculation:

The amounts of metabolites formed were calculated relative to a reference curve stored in the software running the HPLC system. At the level of the calculator, they were converted into pmoles/μl injected. Reference curves exist for testosterone, 5α DHT and 5α androstanediol, the two 5-α-reduced metabolites of testosterone. The amounts were expressed in moles of products formed/mg of homogenate proteins, each test being carried out twice, and the percentage of residual 5-α-reductase activity relative to the control tests was calculated as follows:

$$\% = \frac{\text{Rate of products formed in the presence of inhibitor} \times 100}{\text{Rate of products formed for the controls}}$$

Result

The IC$_{50}$ of inhibition of the 5-α-reductase activity of the human prostate enzyme (PH$_6$) of the products of the invention are given in the following table:

| Example | IC50 |
| --- | --- |
| Example 15 | 5,7.10$^{-7}$M. |
| Example 3 | 7,1.10$^{-8}$M |
| Example 4 | 9,6.10$^{-9}$M |
| Example 13 | 8,7.10$^{-7}$M |
| Example 5 | 9,2.10$^{-8}$M |
| Example 12 | 2,0.10$^{-6}$M |
| Example 11 | 7,7.10$^{-8}$M |
| Example 6 | 3,6.10$^{-8}$M |

CONCLUSION

All these products possess an IC$_{50}$ comprised between 2.0 10$^{-6}$ and 9.6 10$^{-9}$. This inhibitory activity of 5α-reductase makes these products suitable to be used in the treatment of disorders linked to virilism.

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula

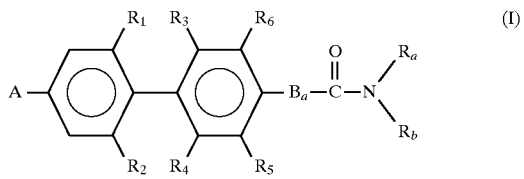

wherein A is selected from the group consisting of carboxy, —CN, —NO$_2$, HONHCO— and a nitrogen heterocycle, B$_a$ is selected from the group consisting of a) —(CH$_2$)$_n$—, n is an integer from 1 to 6, b) —(CH$_2$)$_{n-1}$—CH(Alk)—, Alk is alkyl of 1 to 6 carbon atoms and d) —O—(CH$_2$)$_{n'}$—, n' being an integer from 1 to 6, R$_a$ and R$_b$ are individually selected from the group consisting of hydrogen, alkyl of 1 to 8 carbon atoms, acyl of organic carboxylic acid of 1 to 12 carbon atoms, phenyl, benzyl, diphenylmethyl and trityl or together with the nitrogen to which they are attached form an optionally unsaturated 5 to 6 member heterocycle optionally containing a second —S—, —NH or —O—, R$_1$, R$_2$, R$_3$, R$_4$, R$_5$, and R$_6$ are individually selected from the group consisting of hydrogen, halogen, optionally substituted alkyl of 1 to 8 carbon atoms, alkoxy and alkylthio of 1 to 8 carbon atoms, —NO$_2$, —CN, —CF$_3$, —NH$_2$, mono and dialkyl amino with alkyl of 1 to 8 carbon atoms and

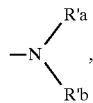

R'a and R'b together with the nitrogen to which they are attached form an optionally unsaturated 5 to 6 member nitrogen heterocycle optionally containing a second nitrogen or —O— or —S— optionally substituted with alkyl of 1 to 4 carbon atoms or R$_4$ and R$_5$ form —CH=CH—CH=CH— and their non-toxic, pharmaceutically acceptable salts with acids or bases.

2. A compound of claim 1 wherein A is carboxy and B$_a$ is selected from the group consisting of —CH$_2$—, —CHCH$_3$— and —OCH$_2$.

3. A compound of claim 1 wherein A is tetrazolyl and B$_a$ is selected from the group consisting of —CH$_2$—, —CHCH$_3$— and —OCH$_2$.

4. A compound of claim 1 wherein R$_a$ and R$_b$ are alkyl of 1 to 8 carbon atoms.

5. A compound of claim 1 wherein R$_a$ and R$_b$ are isopropyl.

6. A compound of claim 1 wherein R$_a$ is hydrogen and R$_b$ is trityl.

7. A compound of claim 1 wherein R$_1$, R$_2$, R$_3$, R$_4$, R$_5$ and R$_6$ are individually selected from the group consisting of hydrogen, chlorine, bromine, iodine, fluorine, methyl, ethyl, propyl, isopropyl, —CN, —NO$_2$, —NH$_2$, dimethylamino, methoxy, ethoxy, methylthio, ethylthio and —CF$_3$ with the proviso that R$_4$ and R$_5$ together may be —CH=CH—CH=CH—.

8. A compound of claim 1 wherein A is carboxy, B$_a$ is selected from the group consisting of —CH$_2$— and —OCH$_2$—, R$_a$ and R$_b$ individually are alkyl of 1 to 8 carbon atoms or R$_a$ is hydrogen and R$_b$ is trityl and R$_1$, R$_2$, R$_3$, R$_4$, R$_5$ and R$_6$ are individually selected from the group consisting of hydrogen, fluorine, chlorine, bromine, iodine, methyl, ethyl, propyl, isopropyl, —CN, —NO$_2$, —NH$_2$, dimethylamino, methoxy, ethoxy, methylthio, ethylthio and —CF$_3$.

9. A compound of claim 1 wherein A is carboxy and B$_a$ is —O—CH$_2$—.

10. A compound of claim 1 selected from the group consisting of

4'-[2-[bis-(isopropyl)-amino]-2-oxoethoxy)-(1,1'-biphenyl)-4-carboxylic acid,

4'-[2-[(bis-(isopropyl)-amino]-2-oxoethoxy]-3', 5'-bis-(isopropyl)-(1,1'-biphenyl)-4-carboxylic acid, 4'-[2-[bis-(isopropyl)-amino]-2-oxoethoxy]-3'-fluoro-5'-nitro-(1,1'-biphenyl)-4-carboxylic acid, 4'-[2-oxo-2-([tribenzyl)-amino]-ethoxy]-(1,1'-biphenyl)-4-carboxylic acid, 3'-fluoro-5'-nitro-4'-[2-oxo-2-[(tribenzyl)-amino]-ethoxy]-(1,1'-biphenyl)-4-carboxylic acid, 4'-[2-[bis-(isopropyl)-amino)-2-oxoethoxy]-2'-ethyl-(1,1'-biphenyl)-4-carboxylic acid, 4'-[2-[bis-(isopropyl)-amino)-2-oxoethoxy]-3'-ethyl-(1,1'biphenyl)-4-carboxylic acid, 4'-[2-[bis-(isopropyl)-amino]-2-oxoethoxy]-2-chloro(1,1'-biphenyl)-4-carboxylic acid, 4'-[2-[bis-(isopropyl)-amino]-2-oxoethoxy]-2-(trifluoromethyl)-(1,1'-biphenyl)-4-carboxylic acid and their addition salts with non-toxic, pharmaceutically acceptable acids and bases.

11. A 5-α-reductase inhibiting composition comprising an amount of a compound selected from the group consisting of a compound of the formula

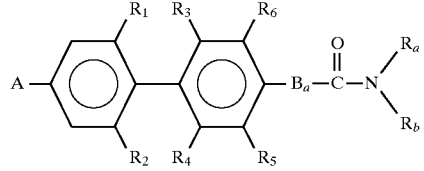

wherein A is selected from the group consisting of carboxy, —CN, —NO$_2$, HONHCO— and a nitrogen heterocycle, B$_a$ is selected from the group consisting of a) single bond, b) —(CH$_2$)$_n$, n is an integer from 1 to 6, c) —(CH$_2$)$_n$, —CH (Alk)—, Alk is alkyl of 1 to 6 carbon atoms and d) —O—(CH$_2$)$_{n'}$—, n' being an integer from 1 to 6, R$_a$ and R$_b$ are individually selected from the group consisting of hydrogen, alkyl of 1 to 8 carbon atoms, acyl of organic carboxylic acid of 1 to 12 carbon atoms, phenyl, benzyl, diphenylmethyl and trityl or together with the nitrogen to which they are attached form an optionally unsaturated 5 to 6 member heterocycle optionally containing a second —S—, —NH or —O—, R$_1$, R$_2$, R$_3$, R$_4$, R$_5$ and R$_6$ are individually selected from the group consisting of hydrogen, halogen, optionally substituted alkyl of 1 to 8 carbon atoms, alkoxy and alkylthio of 1 to 8 carbon atoms, —NO$_2$, —CN, —CF$_3$, —NH$_2$, mono and dialkyl amino with alkyl of 1 to 8 carbon atoms and

R'$_a$ and R'$_b$ together with the nitrogen to which they are attached form an optionally unsaturated 5 to 6 member nitrogen heterocycle optionally containing a second nitrogen or —O— or —S— optionally substituted with alkyl of 1 to 4 carbon atoms or R$_4$ and R$_5$ form —CH=CH—CH=CH— and their non-toxic, pharmaceutically acceptable salts with acids or bases sufficient to inhibit 5-α-reductase and an inert pharmaceutical carrier.

12. A composition of claim 11 wherein the compound is selected from the group consisting of 4'-[2-[bis-(isopropyl)-amino]-2-oxoethoxy)-(1,1'-biphenyl)-4-carboxylic acid, 4'-[2-[bis-(isopropyl)-amino]-2-oxoethoxy]-3', 5'-bis-(isopropyl)-(1,1'-biphenyl)-4-carboxylic acid, 4'-[2-[bis-(isopropyl)-amino]-2-oxoethoxy]-3'-fluoro-5'-nitro-(1,1'-biphenyl)-4-carboxylic acid, 4'-[2-oxo-2-([tribenzyl)-amino]-ethoxy]-(1,1'-biphenyl)-4-carboxylic acid, 3'-fluoro-5'-nitro-4'-[2-oxo-2-[(tribenzyl)-amino]-ethoxy]-(1,1'-biphenyl)-4-carboxylic acid, 4'-[2-[bis-(isopropyl)-amino)-2-oxoethoxy]-2'-ethyl-(1,1'-biphenyl)-4-carboxylic acid, 4'-[2-[bis-(isopropyl)-amino)-2-oxoethoxy]-3'-ethyl-(1,1'-biphenyl)-4-carboxylic acid, 4'-[2-[bis-(isopropyl)-amino]-2-oxoethoxy]-2-chloro(1,1'-biphenyl)-4-carboxylic acid, 4'-[2-[bis-(isopropyl)-amino]-2-oxoethoxy]-2-(trifluoromethyl)-(1,1'-biphenyl)-4-carboxylic acid and their addition salts with non-toxic, pharmaceutically acceptable acids and bases.

13. A method of inhibiting 5-α-reductase in warm-blooded animals comprising administering to warm-blooded animals a 5-α-reductase inhibiting amount of a compound selected from the group consisting of a compound of the formula

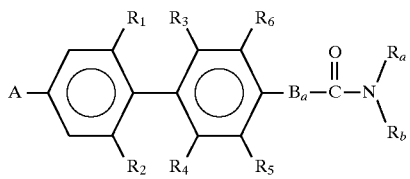

wherein A is selected from the group consisting of carboxy, —CN, —NO$_2$, HONHCO— and a nitrogen heterocycle, B$_a$ is selected from the group consisting of a) —(CH$_2$)$_n$, n is an integer from 1 to 6, b) —(CH$_2$)$_n$, —CH(Alk)—, Alk is alkyl of 1 to 6 carbon atoms and c) —O—(CH$_2$)$_n$'—, n' being an integer from 1 to 6, R$_a$ and R$_b$ are individually selected from the group consisting of hydrogen, alkyl of 1 to 8 carbon atoms, acyl of organic carboxylic acid of 1 to 12 carbon atoms, phenyl, benzyl, diphenylmethyl and trityl or together with the nitrogen to which they are attached form an optionally unsaturated 5 to 6 member heterocycle optionally containing a second —S—, —NH or —O—, R$_1$, R$_2$, R$_3$, R$_4$, R$_5$ and R$_6$ are individually selected from the group consisting of hydrogen, halogen, optionally substituted alkyl of 1 to 8 carbon atoms, alkoxy and alkylthio of 1 to 8 carbon atoms, —NO$_2$, —CN, —CF$_3$, —NH$_2$, mono and dialkyl amino with alkyl of 1 to 8 carbon atoms and

R'$_a$ and R'$_b$ together with the nitrogen to which they are attached form an optionally unsaturated 5 to 6 member nitrogen heterocycle optionally containing a second nitrogen or —O— or —S— optionally substituted with alkyl of 1 to 4 carbon atoms or R$_d$ and R$_5$ form —CH=CH—CH=CH— and their non-toxic, pharmaceutically acceptable salts with acids or bases sufficient to inhibit 5-α-reductase and an inert pharmaceutical carrier.

14. The method of claim 13 wherein A is carboxy and B$_a$ is selected from the group consisting of a single bond, —CH$_2$—, —CHCH$_3$— and —OCH$_2$—.

15. The method of claim 13 wherein A is tetrazolyl and B$_a$ is selected from the group consisting of a single bond, —CH$_2$—, —CHCH$_3$— and —OCH$_2$—.

16. The method of claim 13 wherein R$_a$ and R$_b$ are alkyl of 1 to 8 carbon atoms.

17. The method of claim 13 wherein R$_a$ and R$_b$ are isopropyl.

18. The method of claim 13 wherein R$_a$ is hydrogen and R$_b$ is trityl.

19. The method of claim 13 wherein R$_1$, R$_2$, R$_3$, R$_4$, R$_5$ and R$_6$ are individually selected from the group consisting of hydrogen, chlorine, bromine, iodine, fluorine, methyl, ethyl, propyl, isopropyl, —CH, —NO$_2$, —NH$_2$, dimethylamino, methoxy, ethoxy, methylthio, ethylthio and —CF$_3$ with the proviso that R$_4$ and R$_5$ together may be —CH=CH—CH=CH—.

20. The method of claim 13 wherein A is carboxy, B$_a$ is selected from the group consisting of a single bond, —CH$_2$— and —OCH$_2$—, R$_a$ and R$_b$ individually are alkyl of 1 to 8 carbon atoms or R$_a$ is hydrogen and R$_b$ is trityl and R$_1$, R$_2$, R$_3$, R$_4$, R$_5$ and R$_6$ are individually selected from the group consisting of hydrogen, fluorine, chlorine, bromine, iodine, methyl, ethyl, propyl, isopropyl, —CN, —NO$_2$, —NH$_2$, dimethylamino, emthoxy, ethoxy, methylthio, ethylthio and —CF$_3$.

21. The method of claim 13 wherein A is carboxy and B$_a$ is —O—CH$_2$—.

22. The method of claim 13 wherein the compound is selected from the group consisting of 4'-[2-[bis-(isopropyl)-amino]-2-oxoethoxy)-(1,1'-biphenyl)-4-carboxylic acid, 4'-[2-[bis-(isopropyl)-amino]-2-oxoethoxy]-3', 5'-bis-(isopropyl)-(1,1'-biphenyl)-4-carboxylic acid, 4'-[2-[bis-(isopropyl)-amino]-2-oxoethoxy]-3'-fluoro-5'-nitro-(1,1'-biphenyl)-4-carboxylic acid, 4'-[2-oxo-2-([tribenzyl)-amino]-ethoxy]-(1,1'-biphenyl)-4-carboxylic acid, 3'-fluoro-5'-nitro-4'-[2-oxo-2-[(tribenzyl)-amino]-ethoxy]-(1,1'-biphenyl)-4-carboxylic acid, 4'-[2-[bis-(isopropyl)-amino)-2-oxoethoxy]-2'-ethyl-(1,1'-biphenyl)-4-carboxylic acid, 4'-[2-[bis-(isopropyl)-amino)-2-oxoethoxy]-3'-ethyl-(1,1'-biphenyl)-4-carboxylic acid, 4'-[2-[bis-(isopropyl)-amino]-2-oxoethoxy]-2-chloro(1,1'-biphenyl)-4-carboxylic acid, 4'-[2-[bis-(isopropyl)-amino]-2-oxoethoxy]-2-(trifluoromethyl)-(1,1'-biphenyl)-4-carboxylic acid and their addition salts with non-toxic, pharmaceutically acceptable acids and bases.

23. A compound of the formula
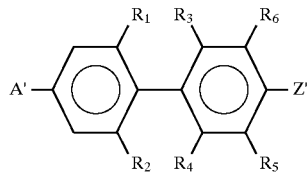 (I')
wherein A' is selected from the group consisting of optionally protected formyl, optionally alkyl esterified carboxyl, CH, nitrogen heterocycle, —NO$_2$, methyl and optionally protected —CH$_2$OH,
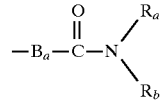
and B$_a$, R$_a$, R$_b$, R$_1$, R$_2$, R$_3$, R$_4$, R$_5$ and R$_6$ are defined as in claim 1.
* * * * *